US008471030B2

(12) United States Patent
Mandal et al.

(10) Patent No.: US 8,471,030 B2
(45) Date of Patent: Jun. 25, 2013

(54) PURIFICATION OF MONTELUKAST USING SIMULATED MOVING BED

(75) Inventors: Arun Kanti Mandal, Mumbai (IN); Kamlesh Jayantilal Ranbhan, Thane (IN); Ganesh Gurpur Pai, Thane (IN); Abhilesh Agarwal, Chicago, IL (US); Rakesh Vikraman Nair Rema, Lisle, IL (US); Asha Oroskar, Oak Brook, IL (US)

(73) Assignee: Orochem Technologies Inc., Naperville, IL (US)

( * ) Notice: Subject to any disclaimer, the term of this patent is extended or adjusted under 35 U.S.C. 154(b) by 275 days.

(21) Appl. No.: 12/928,198

(22) Filed: Dec. 6, 2010

(65) Prior Publication Data
US 2012/0142931 A1     Jun. 7, 2012

(51) Int. Cl.
C07D 215/38     (2006.01)

(52) U.S. Cl.
USPC ................................................. 546/159

(58) Field of Classification Search
USPC ................................................. 546/159
See application file for complete search history.

(56) References Cited

U.S. PATENT DOCUMENTS

| | | | |
|---|---|---|---|
| 2,985,589 A * | 5/1961 | Broughton et al. | 210/676 |
| 5,156,736 A * | 10/1992 | Schoenrock | 210/264 |
| 5,523,477 A | 6/1996 | King | |
| 5,565,473 A | 10/1996 | Belley | |
| 5,614,632 A | 3/1997 | Bhupathy | |
| 7,189,853 B2 | 3/2007 | Sundaram | |
| 7,417,149 B2 | 8/2008 | Turchetta | |
| 7,446,116 B2 | 11/2008 | Bartl | |
| 7,476,748 B2 | 1/2009 | Benovsky | |
| 7,491,719 B2 | 2/2009 | Lustenberger | |
| 7,501,517 B2 | 3/2009 | Overeem | |
| 7,528,254 B2 | 5/2009 | Brand | |
| 7,544,805 B2 | 6/2009 | Alnabari | |
| 7,547,787 B2 | 6/2009 | Shapiro | |
| 7,553,853 B2 | 6/2009 | Overeem | |
| 7,560,559 B2 | 7/2009 | Chou | |
| 7,572,930 B2 | 8/2009 | Wang | |
| 7,589,128 B2 | 9/2009 | Sabo | |
| 7,601,741 B2 | 10/2009 | Benovsky | |
| 7,700,776 B2 | 4/2010 | Hung | |
| 7,829,716 B2 | 11/2010 | Overeem | |
| 2006/0167260 A1 | 7/2006 | Yoshimura et al. | |
| 2008/0194825 A1 | 8/2008 | Perez Andres et al. | |
| 2008/0306270 A1 | 12/2008 | Coppi | |
| 2008/0312270 A1 | 12/2008 | Brown | |
| 2011/0034692 A1 | 2/2011 | Halama et al. | |

FOREIGN PATENT DOCUMENTS

| | | |
|---|---|---|
| EP | 480717 A1 | 4/1992 |
| EP | 737186 B1 | 8/1998 |
| WO | 2004002838 A1 | 4/2004 |
| WO | 2009111998 A2 | 9/2009 |

OTHER PUBLICATIONS

Roman, j Chrom Sc, vol. 49, Aug. 2011, pp. 540-546.*
International Search Report Mailed Aug. 31, 2011 for Corresponding PCT Application PCT/IN2011/000329.
PCT International Search Report and Written Opinion of the International Searching Authority for Corresponding Application PCT/IN2011/000329, Mailed Aug. 31, 2011.
Mahmoud Al Omari, et al., "Effect of light and heat on the stability of Montelukast in solution and in its solid state," Journal of Pharmaceutical and Biomedical Analysis, 2007, pp. 465-471, 45.
Anonymous, Montelukast Sodium—In-Process Revision, Pharmacopeial Forum, (Jan.-Feb. 2010), pp. 1-2, vol. 36(1).
Anonymous, The Semba Octace(TM) Chromatography System, Brochure on web site www.sembabio.com, copyright 2009 to Semba Biosciences, Downloaded Jul. 2010.

* cited by examiner

*Primary Examiner* — D M Seaman
(74) *Attorney, Agent, or Firm* — Richard P Silverman & Assoc., LLC

(57) ABSTRACT

This invention concerns generally with a process for purifying crude pharmaceutical compositions, wherein the crude pharmaceutical composition comprises a sodium salt of Montelukast

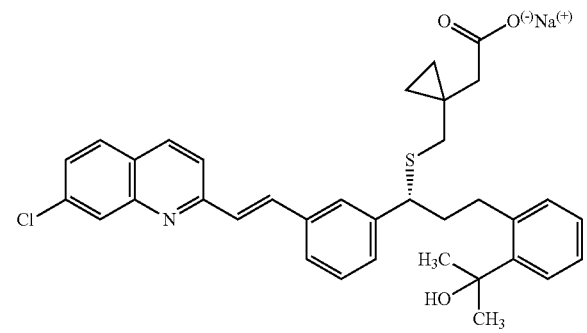

and more particularly relates to a process for the production of pharmaceutically pure preparations of Montelukast sodium using simulated moving bed technology, without requiring an intermediate acid formation step to separate isomers and to remove impurities.

26 Claims, 8 Drawing Sheets

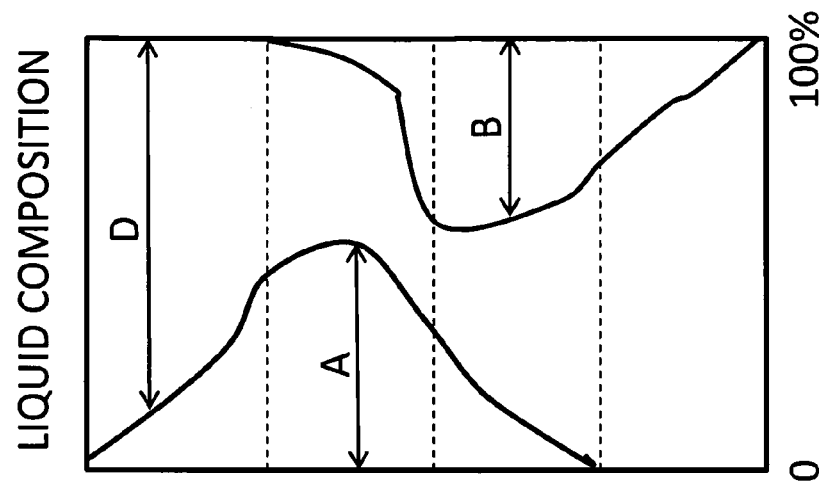
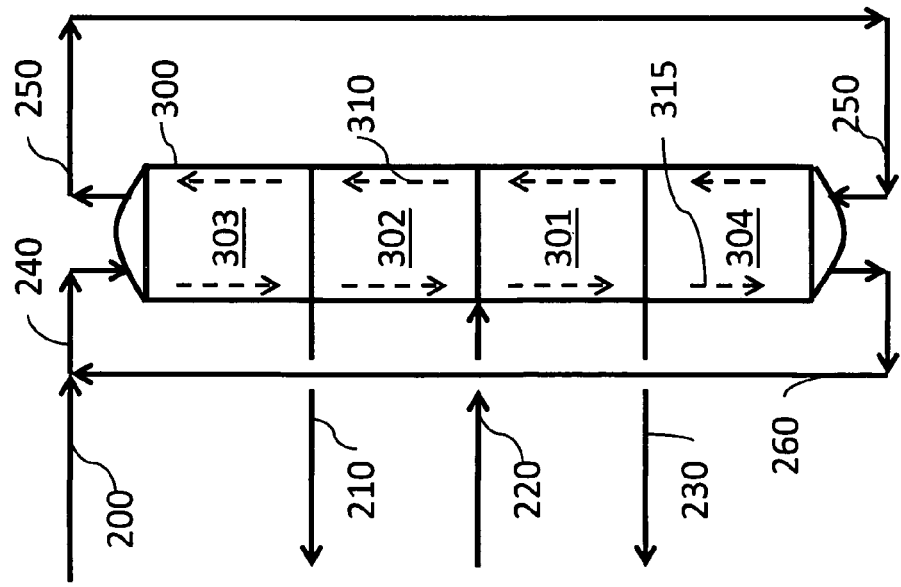
Fig 1

US 8,471,030 B2

PURIFICATION OF MONTELUKAST USING SIMULATED MOVING BED

FIELD OF THE INVENTION

This invention concerns generally with a process for purifying crude pharmaceutical compositions, wherein the crude pharmaceutical composition comprises a sodium salt of Montelukast and more particularly relates to a process for the production of pharmaceutically pure preparations of Montelukast using simulated moving bed technology, without requiring an intermediate acid formation step to separate isomers and remove impurities.

BACKGROUND

Montelukast sodium is used in the treatment of asthma. It is commercialized under the name of SINGULAIR™ (Merck) as oral tablets, chewable tablets and granules. Montelukast sodium has the following structure:

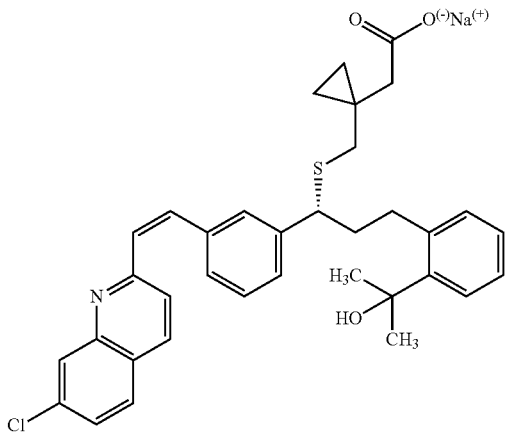

Montelukast Cis-Enantiomer

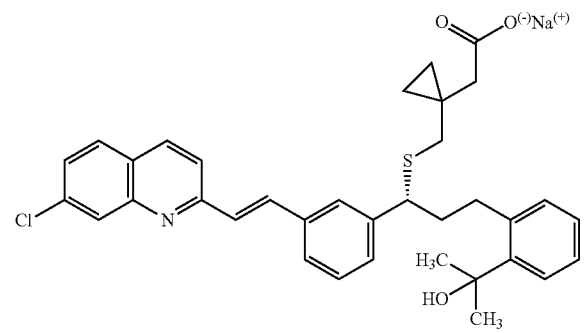

Montelukast is a leukotriene receptor antagonist and an inhibitor of leukotriene biosynthesis. U.S. Pat. No. 5,565,473 discloses and claims the compound and the methods for use. Montelukast is synthesized in a number of ways. The synthesis described in the patent involved methyl esters such as methyl 2-[(3S)-[3-[(2E)-(7-chloroquinolyn-2-yl)ethenylphenyl]-3-hydroxipropyl]benzoate and comprised the coupling between methyl 1-(mercaptomethyl)-cyclopropaneacetate and an appropriate mesilate produced in situ. The methyl ester of Montelukast was hydrolyzed into its acid form and directly transformed into its corresponding sodium salt. The tedious chromatographic purifications of the methyl esters and final products required make the above process unsuitable for large scale production. Additionally, the yields obtained are poor.

EP 737.186 B1 discloses an improved process for the synthesis of Montelukast sodium and dicyclohexylammonium Montelukast, which differed from the process described in EP 480.717 B1 in the use of the dilithium salt of 1-(mercaptomethyl)cyclopropaneacetic acid, instead of the methyl ester for the coupling reaction with the mesylate. The mesylate had the same formula as in EP 480.717 B1 but was added in its crystalline form. The process directly yields Montelukast in its acid form, which is further transformed into its dicyclohexylamine salt, which crystallizes in two different polymorphs. From the purified and crystalline dicyclohexylamine salt, Montelukast in its acid form was recovered by treatment with acid, and then the sodium salt was obtained by treatment of the free acid with a source sodium ions.

Commercially produced Montelukast (the -trans enantiomer) typically include a number of impurities. Examples of the major impurities have the following structures:

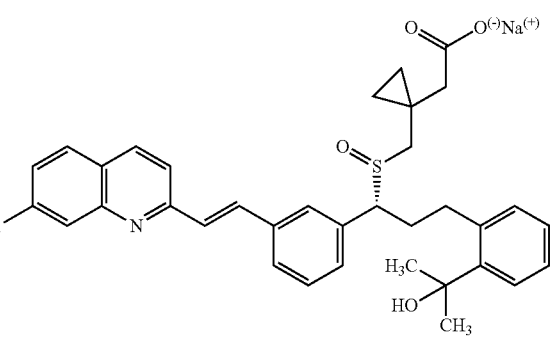

Montelukast Sulfoxide

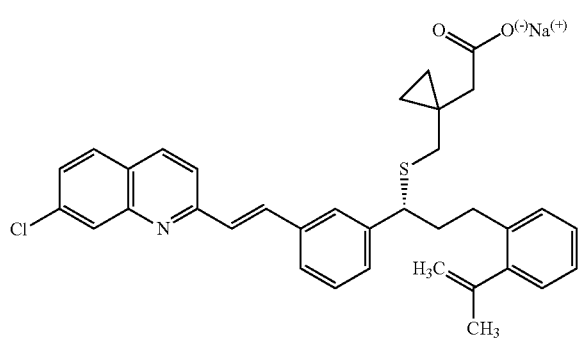

Montelukast Dehydro

U.S. Pat. No. 5,565,473 to BELLEY et al. (see also corresponding EP 0 480 717) discloses a genus of pharmaceutically useful compounds that encompasses Montelukast and salts thereof. Example 161 of BELLEY et al. purports to make the sodium salt of Montelukast via the free acid.

Similarly, WO 95/18107 discloses methods of preparing, inter alia, Montelukast and it salts. Montelukast is converted in situ to the readily isolatable crystalline dicyclohexylamine salt and then subsequently converted to the sodium salt. According to WO 95/18107 this offers a simple and efficient method for the purification of Montelukast and for the preparation of the crystalline Montelukast sodium.

A similar disclosure is found in U.S. Pat. No. 5,523,477 to KING et al. Example 2 shows the formation of Montelukast and conversion into the dicyclohexylamine salt, which is then precipitated. Example 3 shows the conversion of the Montelukast dicyclohexylamine salt to Montelukast sodium by dissolving the solid dicyclohexylamine salt in toluene and adding acetic acid to reform the free acid. Then sodium hydroxide is added to the organic layer containing the acid (Montelukast).

Commercial production of pharmaceutical grade Montelukast sodium typically requires the acidification of the crude Montelukast mixture. The Montelukast is in a free acid form after the final synthesis step. This free acid form is then reacted with a cyclo-aliphatic amine having a basic character. This acid-base reaction is very specific, neutralizing only the Montelukast-trans form. The resulting solution is crystallized to isolate the Montelukast-trans salt in solution. The Montelukast sodium is obtained by the addition of sodium hydroxide in molar excess to the recovered Montelukast-trans salt in solution to replace the cyclo-alaphatic amine group.

A paper entitled, "Effect of light and heat on the stability of Montelukast in solution and in its solid state," by Mahmoud Al Omani, et al., *Journal of Pharmaceutical and Biomedical Analysis*, 45, 465-471, 2007, discloses an number of methods for using a selective HPLC system to measure Montelukast and its major impurities including Montelukast-cis, Montelukast-cis, the Montelukast sulfoxide and the Montelukast dehydro impurities. Montelukast in solution was shown to be unstable when exposed to light leading to the formation of the Montelukast-cis isomer, and disclosed to degrade rapidly in acidic solutions. The disclosed analytical method employed glacial acetic acid and methanol as a mobile phase and octadecyl silane as the stationary phase. A chromatogram produced by this system showed a good separation between Montelukast and the related impurities.

The USP grade acceptance criteria of Montelukast sodium is shown in the following table:

| Component: | Percent (by weight) |
|---|---|
| Montelukast-trans | ** |
| Montelukast-Sulfoxide | 0.1 |
| Montelukast-cis | 0.1 |
| Michael Adducts | 0.1 |
| Ketonic | 0.1 |
| Montelukast-Styrenic Impurities | 0.3 |

** Acceptance criteria: 98.0%-102.0 wt-%, on the anhydrous basis by HPLC

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that retuned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction counter-current to the direction of flow. There are hundreds, if not thousands of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

The continuous nature of SMB operation is characterized by very brief flow stoppages during the port switchovers in successive process steps. However, since all input and output conduits briefly stop at the same time, there are no significant pressure drops or surges in the system. Indexing of mechanical rotors is designed to effect rapid switchovers, even on very large industrial machines. Further, strategy in the design of process configuration is largely dictated by the affinity and release characteristics of bound species to the solid substrate, exclusion properties of unbound species, the bed volume required to obtain separation of by-product, and other factors.

There are more than 200 issued patents on modifications of SMB technology that disclose improvements in separation efficiency generally, or in particular applications, enhanced purity and yield in the final products, or reduction in required volume desorbent. For example, in one variation disclosed in U.S. Pat. No. 5,156,736, separations are performed in a single bed preserving the principles of SMB by interposing at various levels in the bed a series of crossectionally functional collecting and distribution means for adding feedstock and recycled process liquid, collecting raffinate, distributing eluent, and recovering extract product. Equilibrium is established in the system by very precise flow and pressure control.

It is the objective of the invention to replace the current chemical purification steps of acidification of the crude Montelukast, crystallization, isolation, and amine group replacement with a continuous purification process employing simulated moving bed technology.

It is a further object of the invention to reduce or eliminate loss of the key -trans form of Montelukast sodium to the -cis impurity form by carrying out the process in a closed continuous manner with fewer opportunities for exposure to light and acid to reduce the potential loss of the -trans form to the formation of impurities.

It is a still further object of the invention to reduce the Montelukast styrenic impurity by the elimination of an acidifying step in the purification.

SUMMARY OF THE INVENTION

The purpose of the present invention is to present an improved process for the preparation of pharmaceutical grade (USP) Montelukast sodium from crude Montelukast. The inventive process directly converts a crude Montelukast mixture from any synthesis method to a crude Montelukast sodium mixture by reacting the crude Montelukast mixture, typically in a free acid form, in an organic solvent with a inorganic base to provide the Montelukast sodium mixture and passing the crude Montelukast sodium mixture to a simulated moving bed system to recover high purity Montelukast sodium-trans. This direct conversion of the crude Montelukast acid mixture to the corresponding sodium salts followed by the continuous chromatographic separation in a simulated moving bed system removes impurities from a crude Montelukast sodium mixture while avoiding the production of additional impurities in an acidification step of the conventional separation technique. Applicant discovered that using simulated moving bed (SMB) technology provided a continuous process which minimized exposure to light, and eliminated the issue of the sensitivity of the Montelukast sodium-styrenic impurity to acidic conditions. On exposure to light, Montelukast sodium-trans will convert to the -cis form, which must be limited to less that 0.1 wt-% to meet USP specifications.

In one embodiment, the present invention is continuous process for the purification of a crude Montelukast mixture comprising Montelukast-trans, and impurities comprising Montelukast-cis, Montelukast-sulfoxide, Montelukast-styrenic impurities, and other impurities. The continuous process comprises combining the crude Montelukast mixture in an organic solvent with deionized water to provide a feed mixture comprising deionized water, organic solvent, Montelukast sodium-trans, Montelukast sodium-cis, Montelukast sodium-sulfoxide, Montelukast-styrenic impurities and other impurities. The resulting feed mixture has a pH greater than or equal to 8.5. The feed mixture and at least one mobile phase desorbent having a pH of between 8 and 12, are separately passed to a simulated moving bed adsorption system comprising a complex valve system and a plurality of adsorbent beds. The adsorbent beds contain a stationary phase desorbent selective for the separation of Montelukast sodium-trans from at least one of the impurities. In the operation of the simulated bed adsorption system, the stationary phase adsorbent and the at least one mobile phase desorbent are directed to flow in a counter-current manner by the complex valve system to provide a Montelukast sodium-trans rich extract stream, comprising Montelukast sodium-trans and the mobile phase desorbent, and a waste impurity stream comprising the mobile phase desorbent, Montelukast-cis, Montelukast sodium-sulfoxide, Montelukast-styrenic impurities and other impurities. The Montelukast sodium rich extract stream comprises Montelukast sodium-trans, mobile phase desorbent and less than 0.5 wt-% water. The Montelukast sodium-trans rich extract stream comprising Montelukast sodium-trans and mobile phase desorbent is passed to an evaporization zone to recover the mobile phase desorbent and to provide an evaporated extract stream. The evaporated extract stream is stripped with a hydrocarbon solvent to provide a stripped evaporated extract stream, and the stripped evaporated extract is passed to a crystallization zone. In the crystallization zone, the stripped evaporated extract stream is contacted with the hydrocarbon solvent at effective crystallization conditions and a purified Montelukast sodium-trans product is withdrawn.

In another embodiment, the present invention is a continuous process for the purification of an aqueous crude Montelukast sodium mixture comprising Montelukast sodium-trans, impurities and water. The impurities comprise Montelukast sodium-cis, Montelukast sodium-sulfoxide, Montelukast sodium-styrenic impurities, ketonic impurities, and Michael adducts. The process comprises passing the aqueous crude Montelukast sodium mixture to a first stage of a simulated moving bed (SMB) unit and counter currently passing a first portion of a mobile phase stream comprising 100 wt-% methanol to the first stage. The first stage contains a first stage stationary phase adsorbent which is selective for the separation of Montelukast sodium-trans from at least one of the impurities. A first extract stream comprising Montelukast-sulfoxide and a first raffinate stream comprising Montelukast sodium-trans, Montelukast sodium-cis, Montelukast sodium-styrenic impurities, ketonic impurities, Michael adducts, and water are withdrawn from the SMB unit. The first stage raffinate stream is passed to a separation zone to provide an evaporated first raffinate stream. The evaporated first raffinate stream is passed to a second stage of the simulated moving bed unit and counter currently to the passing of the evaporated first raffinate stream, a second portion of the mobile phase stream is passed to the second stage of the simulated moving bed unit. The second stage of the simulated bed unit contains a second stage stationary phase adsorbent selective for the separation of Montelukast sodium-trans from at least one of the impurities to provide a second raffinate stream comprising Montelukast sodium-cis, Montelukast sodium-styrenic impurities, ketonic impurities, Michael adducts and a second extract stream comprising Montelukast sodium-trans. The second extract stream is passed to a drying and crystallization zone operating at effective crystallization conditions to provide a purified Montelukast sodium product.

BRIEF DESCRIPTION OF THE FIGURES

FIG. 1 is a block flow diagram of a single stage of a simulated moving bed unit of the present invention.

DETAILED DESCRIPTION OF THE INVENTION

Figure 2:
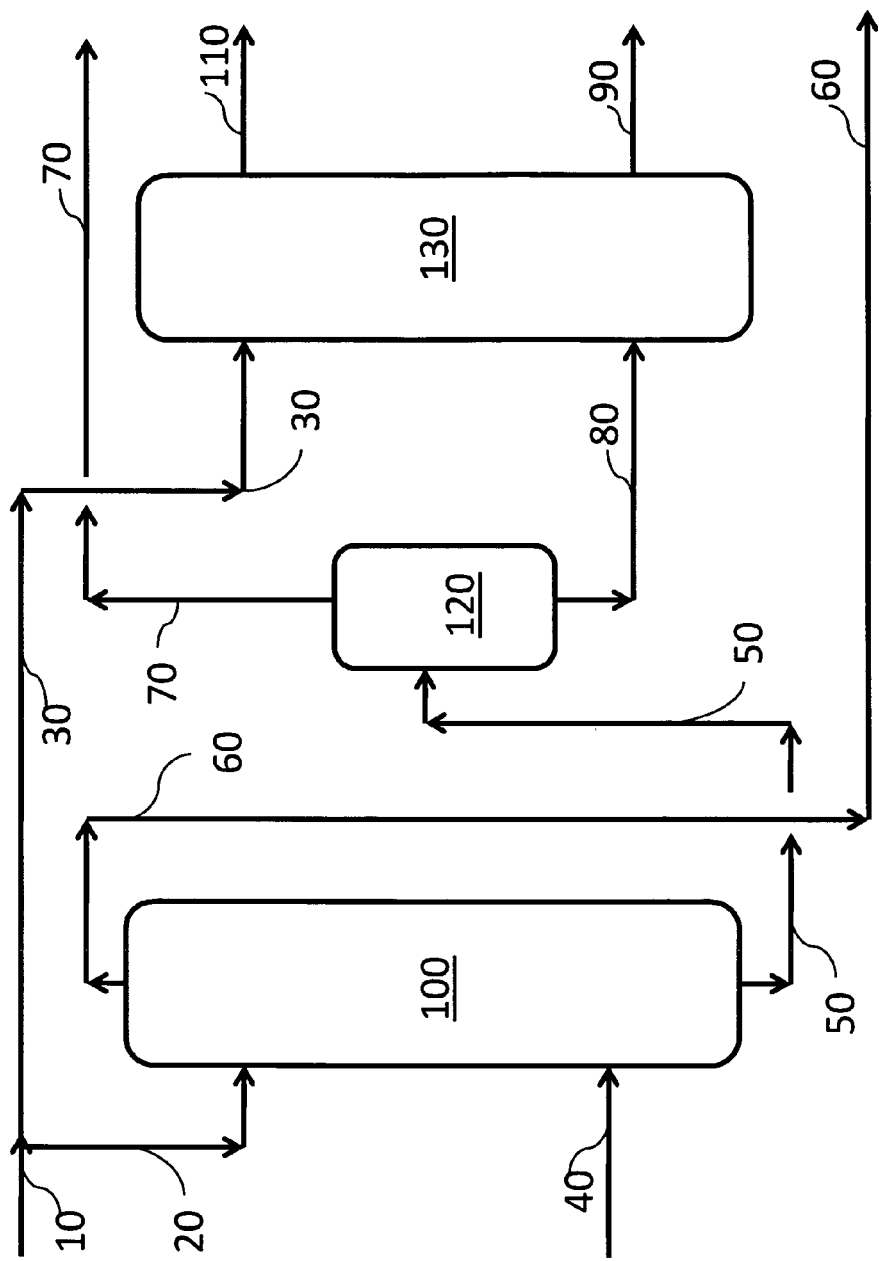
FIG. 2 is a block flow diagram of a multistage simulated moving bed purification system of the present invention.

Conventional preparation of Montelukast sodium has been characterized by reacting crude Montelukast acid mixtures with an organic amine base to form salts which are subsequently purified through a series of multiple crystallizations to provide the Montelukast-trans amine form, before the amine form is acidified in an acidifying step to replace the amine with sodium hydroxide to provide the pure Montelukast sodium-trans form. Applicants recognized that significant loss of the Montelukast-trans form occurred in the final acidification step and sought a Montelukast purification method which did not include the final acidification step, minimized the formation of impurities, and improved the recovery and purity of Montelukast sodium-trans.

The present invention relates to the surprising discovery that crude Montelukast mixtures can be purified by first reacting the crude Montelukast acid mixtures in an organic solvent directly with an inorganic base such as sodium hydroxide, sodium carbonate, sodium bicarbonate, and the like to obtain a crude Montelukast sodium mixture, and subsequently separating the crude Montelukast sodium mixture in a simulated moving bed (SMB) system without employing chemical separation steps. The simulated moving bed route of the present invention replaces the batch process of a series of chemical purification steps, with a continuous process to produce a high yield of acceptable USP pharmaceutical grade Montelukast sodium-trans. Further advantages include, less handling loss than batch processing, and reduced loss of the -trans form in side reactions of the active ingredient by exposure to light and acid.

Crude Montelukast sodium has the following typical composition as shown in Table 1: (Table does not include all components and does not add up to 100 wt-%) Crude Montelukast sodium typically comprises less than about 95 wt-% of Montelukast-trans.

TABLE 1

TYPICAL CRUDE MONTELUKAST COMPOSITION

| COMPONENT: | PERCENT (BY WEIGHT) |
|---|---|
| Montelukast-trans | 94.3-94.9 |
| Montelukast-Sulfoxide | 0.9-1.6 |
| Montelukast-cis | 0.2-0.8 |
| Michael Adducts | 0.1-0.2 |
| Ketonic Impurity | 0.3-0.6 |
| Montelukast-styrenic Impurity | 0.3-1.5 |

The -trans form of Montelukast is the desirable pharmaceutically active form. The other components in the above list are considered to be impurities that must be reduced to the following levels shown in Table 2:

TABLE 2

PHARMACEUTICALLY ACCEPTABLE PURITY LEVELS

| COMPONENT: | PERCENT (BY WEIGHT) |
|---|---|
| Montelukast-Sulfoxide | 0.1 |
| Montelukast-cis | 0.1 |
| Michael Adducts | 0.1 |
| Ketonic Impurity | 0.1 |
| Montelukast Styrenic Impurity | 0.3 |

Because Montelukast sodium-trans was known to be sensitive to light, heat, low pH, and exposure to air, methods were sought that would minimize adverse effects and loss of the active component. Furthermore, the production of the Montelukast sodium-styrenic impurity is sensitive to acidic conditions, and the Montelukast sodium-sulfoxide impurity is formed as an oxidation product of thermal degradation.

The first step in the process of the instant invention is the preparation of a crude Montelukast sodium mixture from a crude Montelukast acid mixture obtained by the synthesis of Montelukast by various routes such as disclosed in U.S. Pat. No. 5,565,473. As formed or isolated, the crude Montelukast acid mixture, is dissolved in an organic solvent such as methanol, a $C_2$-$C_4$ alcohol, or a mixture of acetonitrile and water (ACN/Water). According to the invention, the dissolved crude Montelukast acid mixture in organic solvent is reacted with an inorganic base such as sodium hydroxide, sodium carbonate, sodium bicarbonate, and the like, to convert the crude Montelukast acid mixture to a crude Montelukast sodium mixture to provide the crude Montelukast sodium mixture of sodium salts having a purity of less than about 95 wt-% Montelukast sodium-trans, and having the impurities shown in Table 1, hereinabove. The reaction is carried out while maintaining a pH greater than about 10. Optionally, the organic solvent is removed from the resulting solid crude Montelukast sodium mixture by filtration and washing and stripping to provide a solid crude Montelukast sodium mixture.

The feed stream, or feed mixture, to the SMB system is prepared by combining the crude Montelukast sodium mixture in an organic solvent such as methanol, $C_2$-$C_4$ alcohol, or a mixture of acetonitrile and water, at ambient conditions to completely dissolve the solid crude Montelukast sodium mixture to provide a feed solution. The crude Montelukast sodium mixture may be an isolated solid or a product of the synthesis in an organic solvent which has been directly treated with a sodium inorganic base. The resulting feed solution is further diluted with demineralized water and adjusted to have a pH of from about 8 to about 12 to provide a feed stream having about 10 wt-% or less of the crude Montelukast sodium mixture. Preferably, the feed stream comprises from 2.5 wt-% to 10 wt-% of the crude Montelukast sodium mixture.

In order to minimize the potential for the formation of impurities within the purification process, it is critical to maintain a pH of all of the liquid streams in the process, such as the feed stream, the desorbent or mobile phase, the extract stream, and the raffinate stream, in the alkaline range. Because even mild acidic conditions can accelerate the formation of the styrene impurity, all liquid streams must have a pH in the range between a pH equal to or greater than about 8 and a pH less than or equal to about 12.

Another important parameter in the process of the instant invention is the water content in the mobile phase desorbent. Because the mobile phase desorbent will have an impact on the amount of water which will be recovered in the recovered Montelukast sodium-trans. It was discovered that when the water content of the recovered Montelukast sodium-trans has a water content greater than or equal to 0.5 wt-%, the purified Montelukast sodium product could not be crystallized. Furthermore, too much water in the mobile phase was discovered to have a deleterious effect on desorption of the product and/or the impurities from the stationary phase in the continuous simulated moving bed process.

The solubility of Montelukast sodium-trans and associated impurities in solvents other than methanol is very low. Although it might be possible to carry out the SMB process to some degree with a solvent or mobile phase such as ethanol, isopropanol, butanols, and acetonitrile/water (ACN/water), methanol provides the most cost effective and recoverable alternative. Furthermore, it is preferred that the mobile phase greater than or equal to 99 wt-% methanol, and most preferably the methanol comprises 100 wt-% methanol. The pH of the mobile phase was adjusted to a value of from 8 to 12 by the addition of an inorganic base such as sodium hydroxide, sodium carbonate, and the like.

Temperature and light sensitivity are key issues in minimizing the production of impurities within the SMB process. Accordingly, the SMB process is carried out in the absence of light and at an operating temperature less than or equal to 30° C. In any evaporation or crystallization steps, the temperature of the evaporation or the crystallization stage is maintained less than or equal to 45° C.

To further minimize the potential for impurity formation in the purification process of the instant invention, the concentration of products and impurities in the process streams, were maintained at 10 wt-% or less for the feed stream. More preferably, the concentration of products and impurities in the process streams, were maintained at from 2.5 to 10 wt-% or less for the feed stream, and 2 wt-% or less for the extract and raffinate streams. The feed stream to the SMB system comprised the crude Montelukast sodium mixture diluted to 5 wt-% or less in deionized water having a pH of about 11 by the addition of a base such as sodium hydroxide, sodium carbonate, and the like.

Conventional chromatography presents limitations which are similar to the conventional acidification/crystallization route to purification of the Montelukast sodium. Batch chromatography has the following problems:

a. Difficulty achieving both high purity and low yield,
b. Low adsorbent utilization, c. High product dilution,
d. High solvent consumption, and
e. Potential for yield loss in multiple steps.

Simulated moving bed technology (SMB) represented a substantial opportunity for improvement over both chemical separation steps and conventional chromatography. In SMB, only a partial separation of the solutes is required to obtain high purity with the potential for a yield advantage over batch processing. SMB is a continuous process affording a lower risk of exposure of the active component to loss by side reactions and exposure to light and acid.

The stationary phase of the SMB process provides the separation between the impurities and the active component. Suitable stationary phase adsorbents for the purification of Montelukast sodium-trans from impurities include silica based adsorbents modified with buthyldimethylchlorosilane (C4), octyl (C8), and octadecyl (C18) and basic alumina.

In a series of screening studies to identify and classify potential materials. It was found that when the stationary phase was basic alumina and C18, the desired separation of Montelukast sodium-trans from the impurities could be achieved. The stationary phase comprised particles of an average particle size of between 3 and 300 microns. Preferably, the particle size ranged from 25 microns to 500 microns, and more preferably, the average particle size ranged from 250 to 300 microns. The particles of the stationary phase are irregularly shaped or spherical, or mixtures of irregular shaped and spherical shaped particles.

A critical aspect of the invention was the development of a complementary regime for the selective adsorption of the Montelukast sodium-trans from associated impurities and a complementary desorbent which would be compatible with the adsorbent and which function to remove the impurities from the adsorbent during the full and partial desorption steps in the continuous simulated moving bed cycle. Thus, Montelukast solubility, elution times, separation efficiency, and desorption times were critical factors in the selection of the adsorbent for the stationary phase and the desorbent for the mobile phase of the process. Furthermore, it is believed that particle shape, void space, and surface area of the stationary phase adsorbent material can contribute to the selectivity and performance of the simulated moving bed system.

In another aspect of the invention, it was discovered that in order to obtain a balance of selectivity and recovery in the simulated moving bed system, the crude Montelukast sodium was required to be diluted in aqueous media. Preferably, the feed stream comprising crude Montelukast sodium comprised less than or equal to 10 weight percent crude Montelukast sodium in deionized water, and pH adjusted with inorganic base to a pH of 8 to 12. More preferably, the feed stream comprising crude Montelukast sodium comprised from about 2.5 to 10 weight percent crude Montelukast sodium in deionized water. Most preferably, the feed stream comprising crude Montelukast sodium comprised less than or equal to 5 weight percent crude Montelukast sodium in deionized water. In order to minimize operating problems in the SMB adsorption zone, it is preferred to filter the crude Montelukast sodium mixture feed stream in a suitable filter having 5 micron filter media to avoid introducing suspended particles larger than about 5 microns into the SMB system.

It was discovered in single column tests that when the stationary phase adsorbent was basic alumina, the Montelukast sodium-Sulfoxide impurity was successfully removed from the Montelukast sodium-trans, Montelukast sodium-cis, and Montelukast sodium-styrenic impurities. However, the single column comprising basic alumina was unable to resolve the Montelukast sodium-trans and the Montelukast sodium-styrenic impurity to the level required by USP pharmaceutical specifications. Single column testing of C18 adsorbent (available from Orochem Technologies, Lombard, Ill.), an octadecyl modified silica, having a hydrophobic surface, was found to provide noticeable selectivity for the Montelukast sodium-trans form. The Montelukast sodium-trans form was found to elute faster than all of the other impurities when passed over the C18 adsorbent. Irregular and spherical shaped particles and combinations of irregular and spherical bonded particles were found to provide sufficient selectivity to carry out the SMB process for the purification of crude Montelukast sodium.

The C18 stationary phase adsorbent found to provide the required selectivity and stability for the separation of crude Montelukast sodium-trans from associated impurities were spherical particles having an average particle diameter of from 25 to 500 microns. Preferably, the C18 spherical particles have an average particle diameter of between 25 and 300 microns. Most preferably, the C18 spherical particles have an average particle diameter of between 25 and 60 microns. Furthermore, the C18 spherical particles have an average bulk density (gm/mL) of from 0.4 to 0.6, a surface area ($m^2$/g) of from 450 to 550, and a pore volume of from 0.70-0.90 (mL/g). The C18 spherical particles have a carbon loading (% C) of 15 to 20 wt-%, and a hydrogen (% H) loading of from 2.5-5.5 wt-%. Still further, the C18 spherical particles of the stationary phase desorbent have a solid phase extraction recovery based on Valerophenone of from 55 to 300 micrograms per gram capacity. More preferably, the C18 spherical particles of the stationary phase desorbent have a solid phase extraction recovery based on Valerophenone of from about 60 to about 260 micrograms per gram capacity.

C18 spherical particles used in the SMB process of the instant invention have the following physical properties as shown in Table 3.

TABLE 3

Physical Properties of C18 Adsorbent Spherical Particles

| Property | Unit | 300 μm | 40-63 μm | 25-40 μm |
| --- | --- | --- | --- | --- |
| Surface Area | $m^2$g | 502 | 571 | 513 |
| Pore Volume | mL/g | 0.84 | 0.97 | 0.96 |
| Bulk Density | g/mL | 0.51 | 0.54 | 0.56 |
| Carbon Loading | wt-% | 17.5 | 18.2 | 17.1 |
| Hydrogen Loading | wt-% | 3.5 | 3.3 | 3.2 |
| Valerophenone Capacity | μg/g | 62.52 | 164.65 | 252.85 |

Solid Phase Extraction Recovery Test Procedure

The Solid Phase Extraction Recovery Test with valerophenone, or butyl phenyl ketone, is a test to measure the capacity of the stationary phase adsorbent. C18 sorbent used in the instant invention has porous silica ($SiO_2$) as the support on which Octadecyl silane is covalently bound to make the surface hydrophobic. Any residual Silanol groups (—SiOH) are "endcapped" to remove residual polarity. Capacity test with valerophenone provides a measure of hydrophobicity of the surface which is closely related to surface coverage by the Octadecyl Silane groups. The test procedure is described hereinbelow:

The capacity of the C18 sorbent is usually tested by the adsorption and the elution of valerophenone and hexanophenone in a 5-micron, C18 column. That is, the performance of the C18 sorbent is measured in a column having a 4.6 mm interior diameter and a length of 150 mm, filled with 5 micron C18 sorbent (Available from Orochem, Lombard, Ill.). A detailed description of the protocol for testing the alkylphenone capacity of the adsorbent is described hereinbelow.

Protocol for Alkylphenone Tests

A. Preparation of Calibration Standard

1. Prepare 100 mL solution of 20:80 Acetonitrile:Water by the following method:

a. Measure out 20 mL HPLC grade acetonitrile and 80 mL of deionized water in a glass beaker.

b. Ultrasonicate the 20:80 Acetonitrile:Water solution for 5 minutes prior to further use.

2. Prepare 40 µg/mL solution of a mixed alkylphenones of valerophenone (VP) and hexanophenone (HP) in solution of 20:80 Acetonitrile:Water by the following method:

a. Measure 5.2 µL of valerophenone and 5.8 µL of hexanophenone and dissolve first in 25.74 ml of Acetonitrile.

b. Add deionized water (103 ml) to make final volume up to 128.75 ml solution.

3. Dilute the 40 µg/mL (VP/HP) mixed alkylphenone solution of valerophenone and hexanophenone to to prepare 10 µg/mL, 20 µg/mL and 30 µg/mL solutions using the 20:80 Acetonitrile:Water solution from step 1. For example, in making the 10 µg/mL mixed alkylphenone solution, combine 1 ml of the 40 µg/mL (VP/HP) solution of valerophenone and hexanophenone with 3 ml of the 20:80 acetonitrile:water solution. 40 mL of the 40 µg/mL (VP/HP) solution is required and 10 µg/mL, 20 µg/mL, and 30 µg/mL mixed alkylphenone solutions are prepared by diluting 10 mL portions of the 40 µg/mL (VP/HP) solution of valerophenone and hexanophenone with the 20:80 Acetonitrile:Water solution from step 1.

4. Conduct HPLC runs on the above mentioned four samples to get a calibration curve.

a. Prepare 500 mL solution of 58:42 Acetonitrile:Water. Ultrasonicate the solution for 10 minutes.

b. Use the 5-micron, C18 column (4.6×150 mm) (Available from Orochem, Lombard, Ill.) for detection of the alkylphenones.

c. Prime the column using the 58:42 Acetonitrile:Water solution, until a stable baseline appears.

d. Inject 5 µL of the above-prepared samples. Detect alkylphenones at 254 nm. Measure the area count and plot a graph for further reference.

B. Preparation of Alkylphenone Mixtures

1. Preparation of 10 µg/mL of VP/HP mixtures in 20:80 Acetonitrile:Water solution.

a. Dilute the 40 µg/mL of Valerophenone and Hexanophenone solution from step 3 section A to 10 µg/mL by using 20:80 Acetonitrile:Water solution from step 1 section A.

b. Inject the prepared 10 µg/mL sample in the HPLC and confirm the concentration by comparing against the calibration curve for 20:80 acetonitrile:water. Make a note of the concentration.

2. Preparation of 10 µg/ml of VP/HP mixtures in 40:60 Acetonitrile:Water solution.

a. Make 40 µg/mL solution of VP/HP in 40:60 Acetonitrile:Water. Measure 5.2 µl of Valerophenone and 5.8 µL of Hexanophenone and dissolve first in 51.5 mL of Acetonitrile. Add Water (77.25 mL) to make final volume 128.75 mL. Dilute the mixture to make 10 µg/mL solution using the 40:60 Acetonitrile:Water.

C. Alkylphenone Capacity Test

Step 1. In two bottom fritted 3 cc cartridges fill 200 mg of the C18 sorbent and top frit the cartridges.

Step 2. Place the cartridges such that they remain vertical during the tests. Collect each elute in a separate test tube. Label test tubes in sequence.

Step 2. Prime the cartridges with 3 mL, 100% Acetonitrile. Discard eluates.

Step 3. Prime the cartridges with 3 mL, 15% Acetonitrile in water. Discard eluates.

Step 4. Apply 3 mL of 10 µg/mL alkylphenone mixture prepared in Step 1 of Section B (in 20:80 acetonitrile:water) to cartridges. Allow to gravity flow. Collect eluates, label as #1.

Step 5. Inject portion of eluate #1 into HPLC to detect the alkylphenones on C18 column as mentioned in Step 4 of Section A. Note area count of both alkylphenones, if peaks are detected.

Step 6. Apply 3 mL of 10 µg/mL alkylphenone mixture prepared in Step 1 of Section B (in 20:80 acetonitrile:water) to cartridges. Allow to gravity flow. Collect eluates and label as eluate #2.

Step 7. Inject portion of eluate #2 into HPLC to detect the alkylphenones on C18 column as mentioned in Step 4 of Section A. Note area count of both alkylphenones, if peaks are detected.

Step 8. Apply 3 mL of 10 µg/mL alkylphenone mixture prepared in Step 2 of Section B (in 40:60 acetonitrile:water) to cartridges. Allow to gravity flow. Collect eluates and label as eluate #3.

Step 9. Inject portion of eluate #3 into HPLC to detect the alkylphenones on C18 column as mentioned in Step 4 of Section A. Note area count of both alkylphenones, if peaks detected.

Step 10. Continue Step 8 and Step 9 collecting additional numbered eluate samples (#4, #5, #6, and etc.) until breakthrough occurs; i.e., until peaks are detected.

Step 11. Find the corresponding concentration from the observed area counts.

D. Calculation to Find Capacity in µGrams

From the injections made in Step 1.b and 2.b in Section B find the actual concentration of the alkylphenone mixture.

Add up the total amount of the alkylphenone added to the cartridges until breakthrough occurred using the above concentrations.

Subtract the amount of the alkylphenone at the breakthrough point from the total amount of the alkylphenone added. This provides the capacity of the solid extraction recovery test in µg.

Mobile Phase Desorbent

The mobile phase desorbent for the Montelukast sodium SMB system of the present invention is methanol which has been pH adjusted to a pH of 12 with the addition of sodium hydroxide. Preferably, the methanol purity is greater than or equal to 99 percent by weight methanol and the remaining portion water. More preferably, the methanol comprises 100 percent by weight methanol.

Montelukast sodium-trans is a light sensitive compound which requires special handling in any purification processes. The advantage of a continuous operation for the purification process is the reduced exposure to light. However, the Montelukast-trans must also be protected in solution and in the solid state. For example, it is well known that the Montelukast-trans in an acidic medium can degrade in unacceptable side reactions which reduce the recovery of pure Montelukast-trans. Thus, it is believed that the use of a pH adjusted feed solution and a pH adjusted desorbent or mobile phase desorbent solution having a pH of about 12, minimized the loss of Montelukast sodium-trans, and minimized the production of additional impurities during the simulated moving bed process.

The SMB system of the current invention was arranged for maximum selectivity. The simulated moving bed operation is achieved by use of a plurality of adsorbent beds connected in series and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The operation of the SMB system is carried out at a constant temperature within the adsorbent bed. The feed stream is introduced and components are adsorbed and separated from each other within the adsorbent bed. A separate liquid, the mobile phase desorbent, is used to counter currently displace the feed components from the pores of the adsorbent. Two liquid streams are withdrawn from each bed:

a. An extract stream which is diluted with the mobile phase desorbent b. A raffinate stream which is diluted with the mobile phase desorbent The mobile phase desorbent is subsequently removed from the extract and the raffinate streams by distillation or evaporation and returned to the SMB system.

FIG. 1 illustrates the operation of the present invention. With reference to FIG. 1, a feed stream 220 comprising a most strongly adsorbed species A and a least strongly adsorbed species B is passed to the simulated moving bed SMB unit 300. Continuously and countercurrent to the direction the flow of the feed stream 220, a desorbent stream 200, comprising the mobile phase desorbent, is passed to the simulated moving bed unit 300 via lines 200 and 240. The most strongly adsorbed species A represents one or more components of the crude Montelukast sodium mixture stream, and the least strongly adsorbed species B represents one or more other components of the crude Montelukast sodium mixture stream. The simulated moving bed unit 300 comprises a plurality of adsorbent zones, herein illustrated as zones 301. 302, 303, and 304. The simulated moving bed unit 300 of the present invention comprises at least four adsorbent zones. Each of the adsorbent zones contains one or more adsorbent beds containing the stationary phase adsorbent. The stationary phase adsorbent is chosen to provide the selectivity for the separation of the most strongly adsorbed species A from the least strongly adsorbed species B. The simulated moving bed unit 300 may be operated either in a rejective mode or an extractive mode. In the rejective mode, wherein the least strongly adsorbed species B comprises Montelukast sodium-trans and the most strongly adsorbed species A comprises Montelukast sodium-Styrenic impurities, the Montelukast sodium-trans is withdrawn from the simulated moving bed unit 300 in raffinate stream 230. In the rejective mode, the extract stream 210 which is withdrawn from the simulated moving bed unit 300 comprises Montelukast sodium-Styrenic impurities. When the simulated moving bed is operated in the extractive mode, the extract stream 210 comprises Montelukast sodium-trans, and the raffinate comprises Montelukast sodium-cis, and any remaining impurities. During the continuous operation of the simulated moving bed unit 300 the stationary phase is considered to be circulating continuously, in a closed cycle, and moves up the adsorbent beds from the bottom zone 304, through zones 301, 302, and 303 to the top. Individual adsorbent zones (301, 302, 303, and 304) arranged in series and are cycled in a manner wherein the stationary phase flows in a direction shown by line 250 which is countercurrent to the direction of the flow of the desorbent or mobile phase shown as lines 240 and 260. A complex valve system (not shown) moves the flows of feed, mobile phase, extract and raffinate streams to each of the adsorbent zones in a serial manner such that in each zone, the feed stream 220 enters counter currently to the direction of the mobile phase desorbent stream 240, and the extract stream 210 is withdrawn counter currently to the raffinate stream 230. During the process of the instant invention, zone 301 functions to adsorb the most strongly adsorbed species A, zone 302 functions to desorb the least strongly adsorbent species B, zone 302 at the top functions to desorb the most strongly adsorbed species A, zone 304 provides a partial desorption of the mobile phase 260. During the continuous operation of the simulated moving bed unit 300, the liquid composition profile showing the corresponding liquid composition within the simulated moving bed 300 at each of the zones 301-304 for the most strongly adsorbed species A, the least strongly adsorbed component B, and the mobile phase D.

The process of the present invention may be carried out in one or more SMB stages to provide the high purity Montelukast sodium-trans product. Each of the zones within each SMB stage may contain one or more beds of stationary phase adsorbent in order to provide sufficient retention time in each of the zones to achieve the desired separation.

In one embodiment, the invention is a two-stage SMB continuous process system for the purification of a crude Montelukast sodium mixture as shown in FIG. 2. Prior to processing, crude Montelukast mixture derived from any suitable synthesis scheme is reacted with an inorganic base such as methanolic sodium hydroxide to form crude Montelukast sodium and diluted in deionized water and pH adjusted with sodium hydroxide to a pH of about 12 to form the SMB feed stream. The feed stream comprises water and the crude Montelukast sodium mixture which includes Montelukast sodium-trans, Montelukast sodium-cis, and other impurities including Montelukast sodium-sulfoxides, ketonic impurities, Montelukast sodium-styrenic impurities, and Michael adducts. The feed stream comprises 2.5 to 10 wt-% crude Montelukast sodium mixture. Preferably, the crude Montelukast sodium mixture is diluted to less than 10 weight percent Montelukast in deionized water. More preferably, the crude Montelukast sodium mixture is diluted to equal to or less than 5 weight percent crude Montelukast sodium mixture in the deionized water. Dilution of the crude Montelukast sodium mixture in the feed stream is required to obtain the selectivity in SMB zone 100 for the Montelukast sodium-Styrenic impurity. With reference to FIG. 2, a mobile phase desorbent stream 10 comprising methanol adjusted with sodium hydroxide to a pH of about 12 is passed to the first simulated moving bed (SMB) zone 100. It is necessary to use 99-100 wt-% methanol in order to minimize the amount of moisture in the final Montelukast-trans product. SMB zone 100 contains four zones, each zone containing a stationary phase adsorbent. The feed stream 40 is passed to the SMB zone 100. The first SMB zone 100 is operated in a rejective mode to produce a first extract stream 60 comprising the Montelukast sodium-styrenic impurity, and to provide a first raffinate stream 50 comprising water, methanol, Montelukast sodium-trans, Montelukast-cis and Montelukast-sulfoxides. The first extract stream 70 is passed to waste disposal. Optionally, methanol in the first extract stream may be recovered and recycled to provide additional mobile phase desorbent (not shown). The first raffinate stream 50 is withdrawn from the first SMB zone 100 and passed to a separation zone 120 comprising an evaporization or a distillation step. In the separation zone 120, a portion of the methanol and water are separated from the first raffinate stream 50 to provide an evaporated stream 80. The separation is performed at a separation temperature less than or equal to about 50° C. and a separation pressure equal or below atmospheric pressure and effective to perform the separation. The first raffinate stream 50 has a water content which ranges from about 5 to about 15 wt-percent. The evaporated stream 80, comprising less than about 5 wt-% water, is passed to the second SMB zone 130. The second SMB zone 130 is operated in an extractive mode to provide a second extract stream 110 comprising purified Montelukast sodium-trans and a second raffinate stream 90 comprising the impurities: Montelukast sodium-cis and Montelukast-sulfoxides. The second SMB zone 130 contains at least four zones, each zone containing a stationary phase adsorbent. In the second SMB zone the mobile phase is counter currently contacted with the stationary phase adsorbent as the second SMB zone is cycled as shown in FIG. 1 by a complex vale system (not shown). The second raffinate stream 90 is passed to waste disposal, or optionally sent to methanol recovery (not shown) to recover at least a portion of the methanol, which may be returned to the SMB as the mobile phase desorbent following appropriate removal of water and pH adjustment. The second extract stream 110, comprising Montelukast sodium-trans, is withdrawn from the second SMB zone. The second extract stream 110 having a negligible amount of moisture (less than about 0.1 wt-percent) is passed to a drying and crystallization zone (not shown) wherein the second extract stream can be evaporated to dryness at a temperature less than 45° C. to provide an evaporated second extract stream. Optionally, the second extract stream or the evaporated second extract stream is passed to a crystallization zone (not shown) wherein the evaporated second extract stream is stripped with a hydrocarbon solvent and crystallized at effective crystallization conditions to provide the final solid Montelukast sodium-trans product which meets or exceeds the USP specification for Montelukast sodium. Crystallization of the final solid Montelukast sodium-trans product is performed in a crystallization zone in the presence of an additional solvent such as heptane, hexane, toluene and mixtures thereof at an effective crystallization temperature of between 10-15° C., and dried under vacuum conditions at a drying temperature of 50 to 55° C. The drying and crystallization steps are carried out in an enclosed system in the absence of daylight or white light to minimize the formation of the -cis form of Montelukast. The USP specification requires a 98% to 102 wt-% based on an assay by HPLC on an anhydrous basis. The process of the instant invention achieves a final purity of 99.5 wt-% with all known and unknown impurities within the USP specification and assay 98% to 102 wt-% by HPLC on anhydrous basis.

Figure 5:
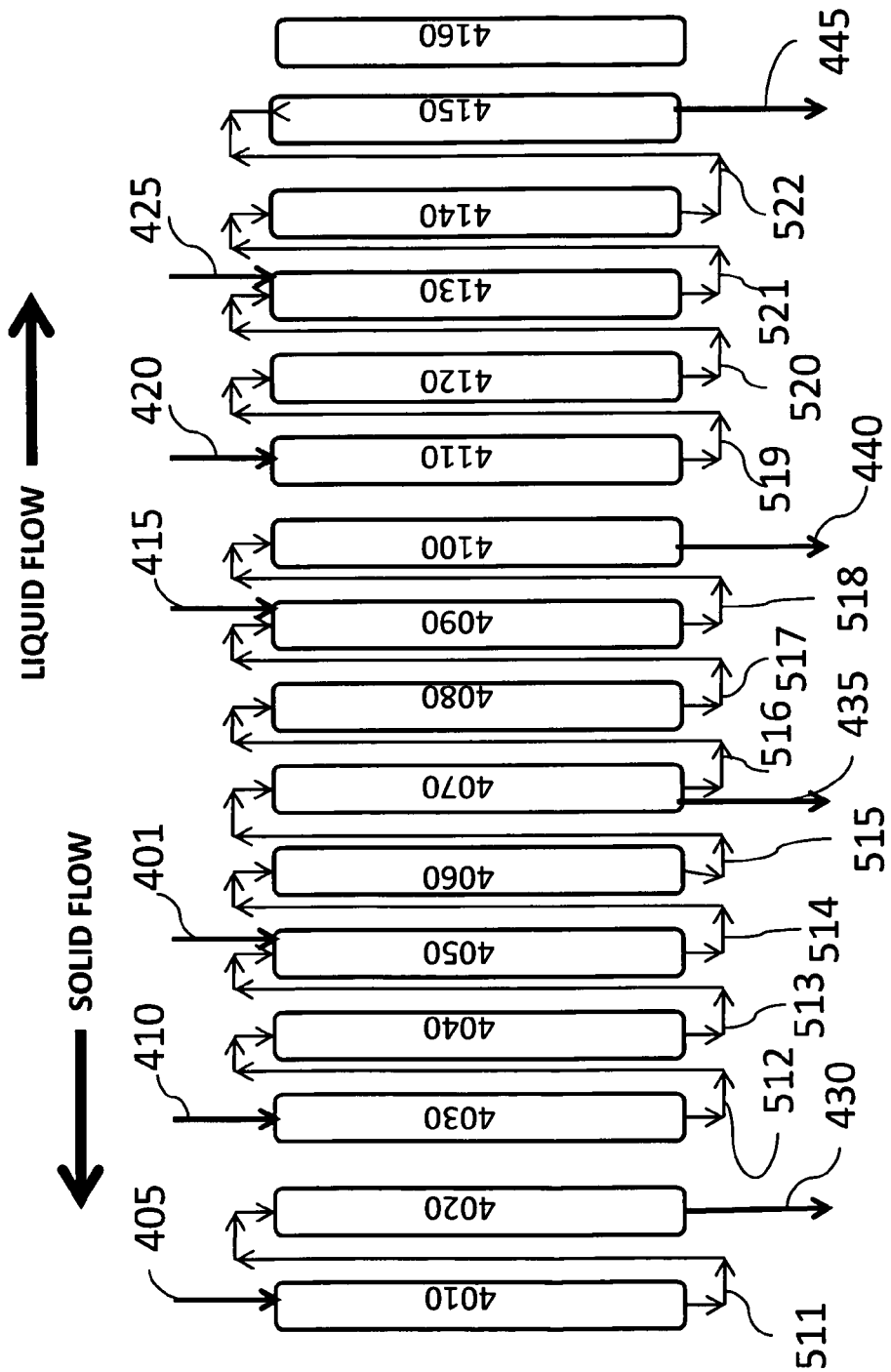
FIG. 5 is a block flow diagram of an integrated simulated moving bed system of the present invention.

In another embodiment, the invention is an integrated, multistage, continuous SMB system of the instant invention for the purification of crude Montelukast sodium as shown in FIG. 5. In the scheme according to FIG. 5, the complex valve system (not shown) operates two SMB stages to provide a continuous SMB system. With reference to FIG. 5, the SMB system comprises a series arrangement of 16 individual adsorbent zones (numbered 4010 through 4160). The individual adsorbent zones (4010 through 4160) contain the stationary phase adsorbent. According to the process of the invention, a feed stream in line 401 comprising the crude Montelukast sodium mixture diluted to a concentration of less than 10 wt-% in deionized water and adjusted to a pH of between 8 and 12 is passed to the top of adsorbent zone 4050. The mobile phase desorbent comprising 100 wt-% methanol is passed to the top of adsorbent zone 4010 via line 405 and to the top of adsorbent zone 4090 via line 415. A primary or first raffinate stream 445 comprising impurities which elute faster than, or before the Montelukast sodium-trans peak are withdrawn from the bottom of adsorbent zone 4150, and passed to waste disposal. A first extract stream 430 comprising impurities which elute after the Montelukast sodium-trans peak is withdrawn from the bottom of adsorbent zone 4020 and passed to waste disposal. An intermediate raffinate stream 435 comprising Montelukast sodium-trans, mobile phase desorbent and water is withdrawn from the bottom of adsorbent zone 4070. If an optional separation or evaporation zone (not shown) is required to remove water, an evaporated intermediate raffinate stream is returned to the top of adsorbent zone 4130 in line 425. When the optional evaporization zone is not required, the intermediate raffinate stream 435 is returned to the top of adsorbent zone 4130 in line 425. The optional evaporization zone operates at an evaporation temperature less than about 50° C. and an evaporation pressure below atmospheric pressure or at vacuum conditions sufficient to provide an evaporated intermediate raffinate stream in line 425 having a crude Montelukast sodium mixture concentration of from 2.5 wt-% to 10 wt-% in water. A second extract stream 440 comprising Montelukast sodium-trans and mobile phase desorbent is withdrawn from adsorbent zone 4100. The second extract stream 440 is essentially free of water; that is, the second extract stream comprises less than or equal to about 0.5 wt-% water. The second extract stream 440 is passed to a second evaporation zone for the removal and recovery of the mobile phase desorbent to provide an evaporated second extract stream. The second evaporization zone operates at a second evaporization zone temperature less than about 50° C. and a second evaporation pressure at a vacuum pressure effective to remove essentially all of the mobile phase desorbent. The evaporated second extract stream is passed to a conventional crystallization zone, wherein the pure Montelukast sodium-trans is further stripped with a hydrocarbon solvent such as hexane, heptane, or toluene and crystallized with a suitable solvent such as hexane, heptane, or toluene at an effective crystallization temperature of about 10-15° C., filtered and dried at a reduced pressure and a drying temperature of 50 to 55° C. to provide a purified solid Montelukast sodium-trans product. The evaporization and crystallization zones are not shown. During the operation of the SMB unit the liquid flows move from left to right, cascading from the bottom of adsorbent zone 4010 to the top of adsorbent zone 4020 in line 511; from the bottom of adsorbent zone 4030 in line 512 to the top of adsorbent zone 4040, from the bottom of adsorbent zone 4040 in line 513 to the top of adsorbent zone 4050, from the bottom of adsorbent zone 4050 in line 514 to the top of adsorbent zone 4060, from the bottom of adsorbent zone 4060 in line 515 to the top of adsorbent zone 4070, from the bottom of adsorbent zone 4070 in line 516 to the top of adsorbent zone 4080, from the bottom of adsorbent zone 4080 in line 517 to the top of adsorbent zone 4090, from the bottom of adsorbent zone 4090 in line 518 to the top of adsorbent zone 4100; from the bottom of adsorbent zone 4110 in line 519 to the top of adsorbent zone 4120, from the bottom of adsorbent zone 4120 in line 520 to the top of adsorbent zone 4130, from the bottom of adsorbent zone 4130 in line 521 to the top of adsorbent zone 4140, from the bottom of adsorbent zone 4140 in line 522 to the top of adsorbent zone 4150. Adsorbent zone 4160 is idle during this time segment. In the continuous operation of the SMB system, the adsorbent zones remain stationary, but valve positions are moved by the complex valve system (not shown) in a manner which simulates the movement or flow of the solid or stationary phase from the right to the left in a direction which is counter current to the direction of the flow of the mobile phase.

The invention will be further be illustrated by the following non-limiting examples.

Feed Preparation

Conversion of Montelukast (crude) to crude Montelukast sodium mixture: Methanolic sodium hydroxide 6.8 grams (0.17 mole in 100 ml methanol) was added slowly to (Crude) Montelukast 100 grams (0.17 mole) dissolved in 400 ml of methanol at 25-30° C., under stirring keeping the temperature at 0-5° C. to adjust the pH of the contents to 10.3-10.6. Stirring was continued for another 30 minutes at the temperature of 0-5° C. Temperature was then gradually increased to 25-30° C. to obtain a clear reaction solution. The clear reaction solution was charcolised by adding 10 grams activated charcoal and reaction solution was filtered through a 0.45 micron filter. The filter bed was washed with 100 ml methanol and filtrate was collected. Methanol was removed from the filtrate under reduced pressure at the temperature not exceeding 50-55° C. The resulting solids were further stripped with heptane (2×50 ml) to remove any remaining methanol. As a final step, 500 ml heptane was added under stirring and the stirring was continued for an hour at 25-30° C. The resulting precipitated crude Montelukast sodium mixture was further cooled to 10-15° C. and product was filtered off and dried under vacuum at 50-55° C. The yield of solid crude Montelukast sodium mixture was 101 grams.

Crude Montelukast Sodium Mixture Feedstock Preparation:

50 grams of solid crude Montelukast sodium mixture as prepared hereinabove, was added to a flask containing 1.0 liter of 100 wt-% methanol while stirring at ambient temperature (25-30° C.) until the solid crude Montelukast sodium mixture completely dissolved. To the resulting solution 1.0 liter of DM (demineralized) water was added while stirring was continued for another half an hour at ambient temperature (25-30° C.). The resulting solution was filtered through 0.45 micron filter to provide a crude Montelukast sodium feed solution for the SMB.

Methanol Mobile Phase Desorbent preparation:

5.0 Liters of 100 wt-% Methanol was added to a flask. The pH of the Methanol was adjusted to 8-12 by adding a solution of sodium hydroxide in methanol [prepared by stirring sodium hydroxide pellets in methanol at ambient temperature (25-30° C.) followed by sonication]. The resulting pH adjusted methanol was used as the mobile phase desorbent for the SMB separation.

Example 1

Method Development

A chromatographic column was prepared for high pressure liquid chromatography (HPLC) column having an inside diameter of 4.6 mm×150 mm in length of packing of 3 micron adsorbent particles to evaluate stationary phase performance of various adsorbents for use in a simulated moving bed process. The mobile phase was an 83:17 by weight composition of acetonitrile (ACN):$NaH_2PO_4$ buffer under isochratic conditions, at a constant temperature, and a constant flow rate. The UV spectrophotometric analysis was carried out at a wave length of 225 nm.

The crude Montelukast sodium mixture composition as measured by HPLC comprised the following components shown in Table 4:

TABLE 4

Actual Crude Montelukast sodium Mixture Sample Analysis (Amounts do not include all components and therefore does not add to 100%)

| Component: | Percent (BY WEIGHT) |
|---|---|
| Montelukast-trans | 94.8 |
| Montelukast-Sulfoxide | 1.49 |
| Montelukast-cis | 0.2 |
| Michael Adducts | 0.12 |
| Ketonic Impurity | 0.6 |
| Montelukast-Styrenic Impurity | 0.48 |

The feed flow rate of the crude Montelukast sodium mixture to the chromatographic column of Example 1 was 1 ml/minute. The crude Montelukast sodium feed to the HPLC column was diluted in deionized water to provide a stream having 5 percent weight crude Montelukast sodium mixture. HPLC chromatograms of the crude Montelukast sodium feed stream indicated that basic alumina and C18 provided acceptable separation between the Montelukast sodium-trans species and the associated impurities listed hereinabove in Table 3.

Example 2

Process Development

Figure 3:
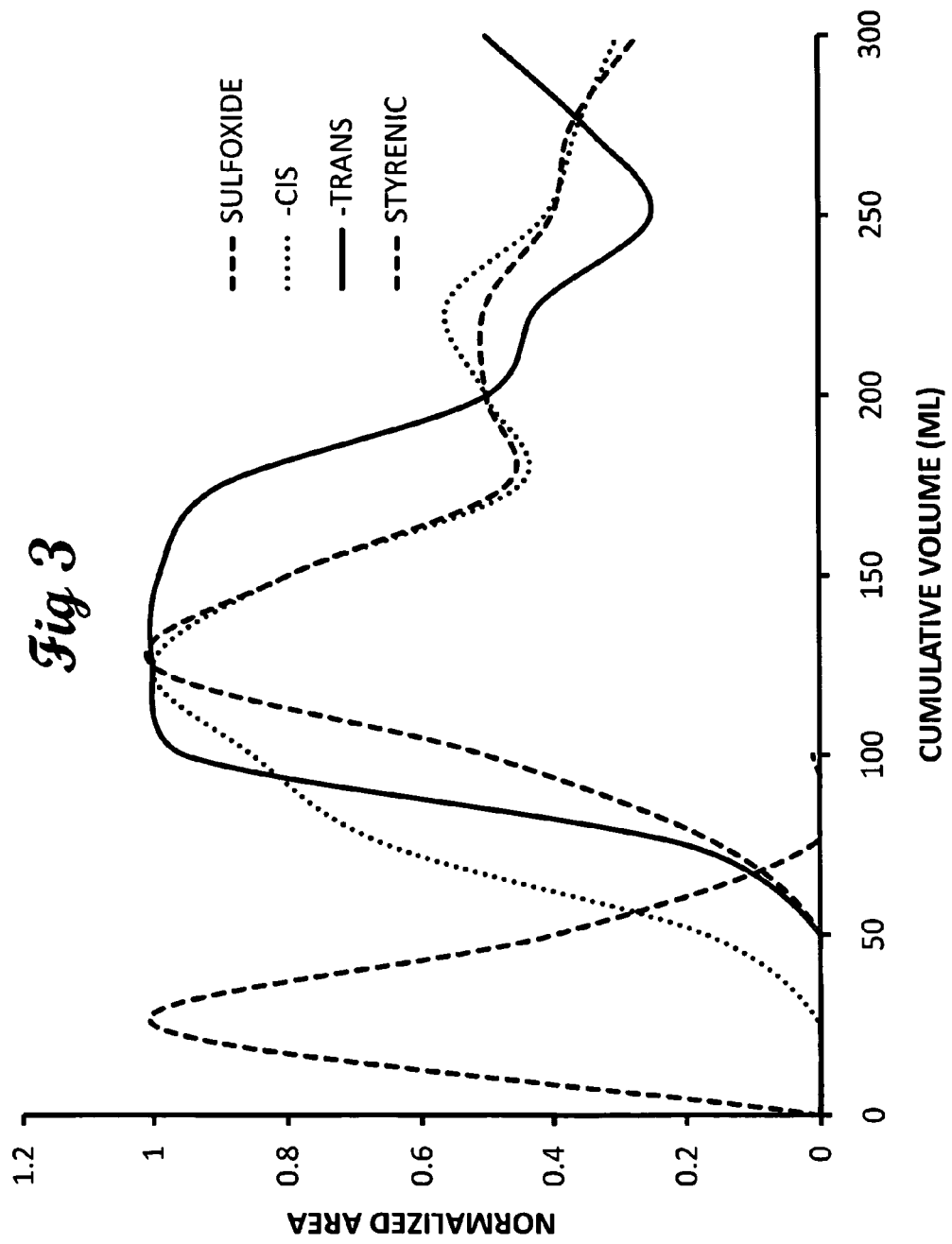
FIG. 3 is an elution profile of Montelukast and impurities on a 300 micron basic alumina irregular adsorbent.

A chromatographic column was prepared for high pressure liquid chromatography (HPLC) for use in establishing the elution profile of the major components of crude Montelukast. The chromatographic column was packed with a 22 mm I.D.×250 mm long bed of column packing comprising 300 micron irregular shaped particles of basic alumina which functioned as the static phase (S.P.). The mobile phase desorbent (M.P.) was 100 wt-% methanol (having a pH adjusted with sodium hydroxide to about 12, as prepared hereinabove). A 2 ml feed stream comprising 5 wt-% crude Montelukast sodium mixture and the remainder deionized water was charged to the chromatographic column. The charge flow rate was 5 ml per minute. The elution profile of the components of the crude Montelukast sodium mixture on irregular 300 micron basic alumina is shown in FIG. 3. FIG. 3 shows that the Montelukast sodium-Sulfoxide impurity was selectively removed from the Montelukast-trans, Montelukast sodium-cis, and Montelukast sodium-Styrenic impurities. However, the basic alumina stationary phase was not able to achieve a purity which meets USP pharmaceutical specification.

Example 3

Pulse Test of C18 Stationary Phase

Figure 4:
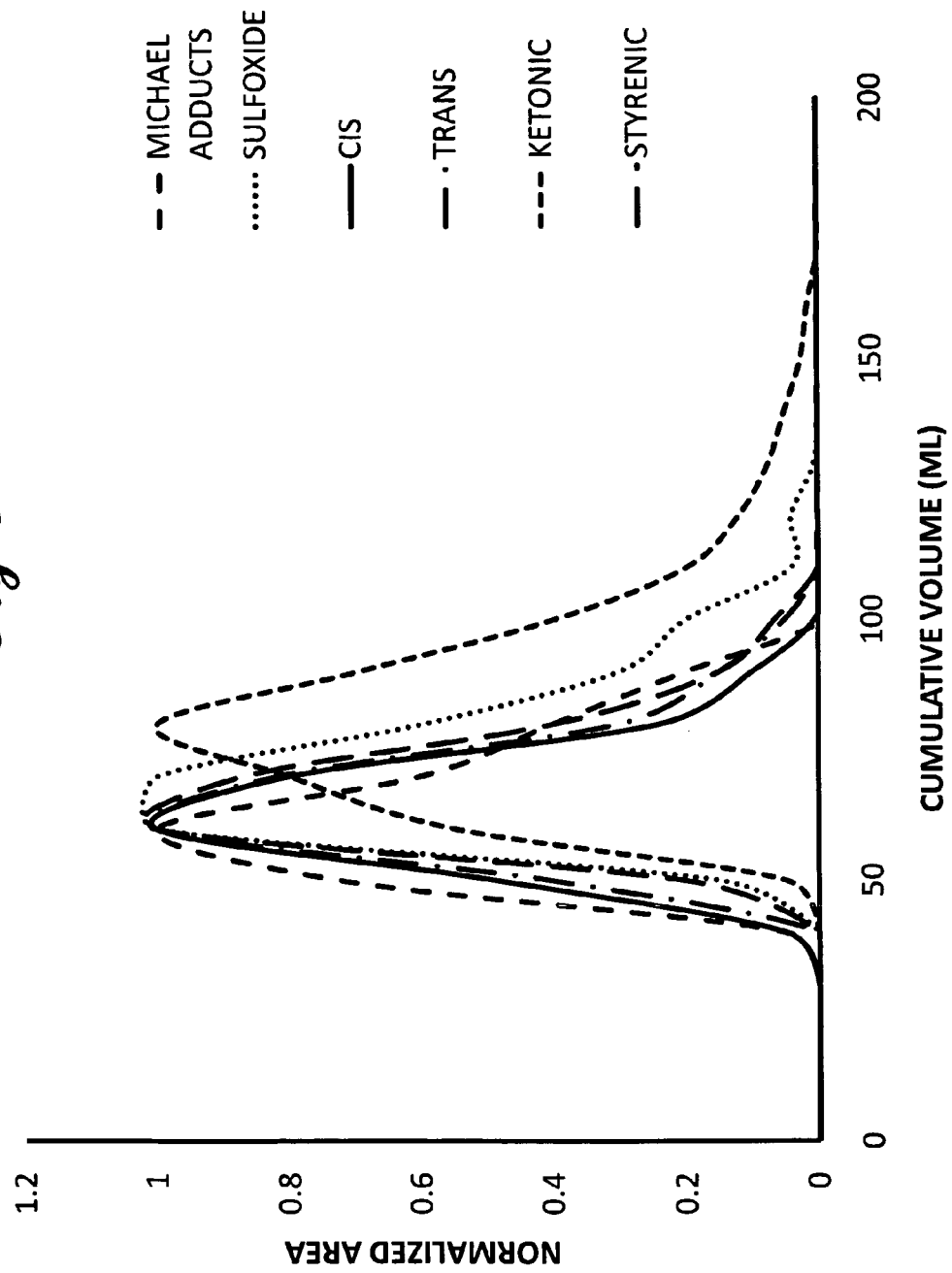
FIG. 4 is an elution profile of Montelukast and impurities on a 300 micron C18 irregular adsorbent.

A chromatographic column was prepared for high pressure liquid chromatography (HPLC) as in Example 2 for use in establishing the elution profile of the major components of crude Montelukast sodium mixture over a C18, an octadecyl modified silica, Stationary Phase. The C18 particles were irregular shaped and 300 microns in size. The procedure of Example 2 was repeated for the C18 stationary phase adsorbent. The elution profile for the major components over the C18 stationary phase is shown in FIG. 4. FIG. 4 shows that the Montelukast sodium-Sulfoxide impurity and the Montelukast sodium-Styrenic impurity elute after the Montelukast-trans peak with noticeable selectivity in this single column test. Similarly, the selectivity between Montelukast sodium-cis and Montelukast sodium-trans was also observed.

Example 4

Simulated Moving Bed Technology

Single Stage SMB Separation

Figure 6:
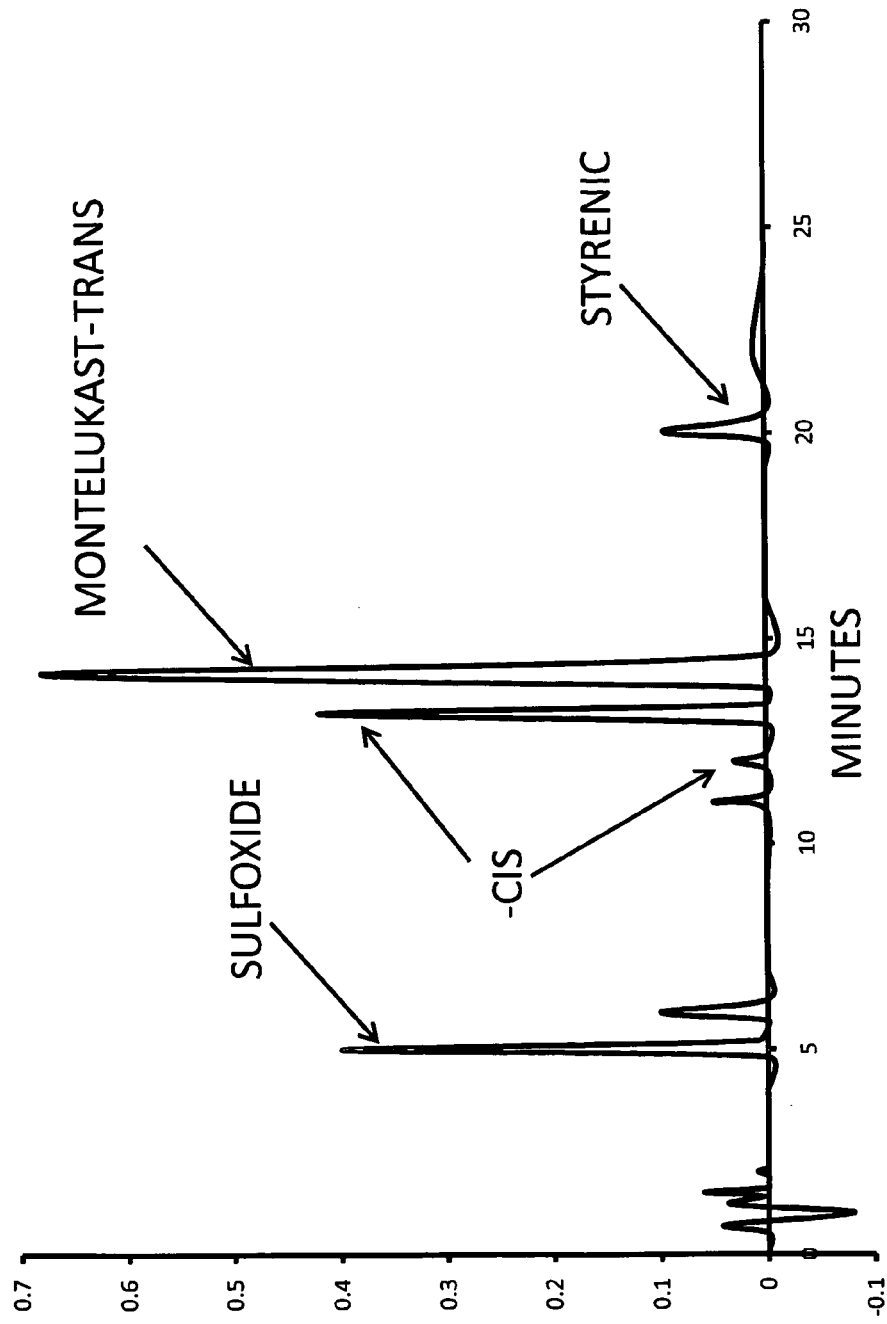
FIG. 6 is an elution profile of the major impurities in crude Montelukast sodium shown relative to the Montelukast sodium-trans peak.

A reverse phase, four zone SMB system using a control and valve switching unit (SMB unit available from Semba Biosciences, India) was arranged with 8 columns, each column containing a packed zone of 20 mm I.D.×250 mm in length and packed with 300 micron irregular shaped C18 adsorbent particles. C18 was an octadecyl modified silica, described hereinabove available from Orochem Technologies, Lombard, Ill. The single stage SMB unit was configured to operate in a 1-4-3 mode; i.e., 4 columns for zone 2, 3 columns for zone 1 and 1 column for zone 4. The mobile phase desorbent was 100 wt-percent methanol having a pH of 12 as prepared hereinabove, adjusted by the addition of sodium hydroxide. The crude Montelukast sodium feed mixture had impurities that have retention orders as shown in FIG. 6 relative to the Montelukast sodium-trans peak. The Montelukast sodium-Styrenic impurities eluted after, or more slowly than the Montelukast sodium-trans, while the Montelukast sodium-cis and Montelukast sodium-sulfoxide and Michael Adducts (not shown) impurities eluted before, or more quickly than the Montelukast sodium-trans peak.

The single stage was operated in a rejective mode to collect the Montelukast sodium-trans form in the raffinate stream. Impurities eluting slower than Montelukast sodium-trans; that is, eluting after the Montelukast-trans sodium peak, were extracted from the SMB unit and removed in the extract stream. The single stage SMB unit provided a raffinate stream comprising about 98 wt-% Montelukast sodium-trans at a recovery about 95%.

Example 5

Single Stage Separation Purity

A 100 g sample of the raffinate stream from Example 4 was analyzed before and after crystallization. Montelukast sodium-Styrene impurity level of the raffinate stream was found to about 0.2% wt-pct. The raffinate was charged to a clean dry flask and methanol was removed by maintaining a temperature of less than 50° C. at reduced pressure. The remaining raffinate material was stripped twice with heptane by adding for each stripping 50 ml of heptane and maintaining the reduced pressure at a temperature less than 50° C. In a final step, 400 ml of heptane were added to the remaining contents of the flask while stirring for 1 hour at a temperature of 25-30° C. The contents of the flask were cooled to a temperature of 10-15° C., filtered to recover a solid, and the resulting solid was dried at a pressure below atmospheric pressure and a drying temperature of between 50 and 55° C. Crystallization of the raffinate stream did not result in any improvement in the purity of the recovered Montelukast sodium-trans.

Example 6

Simulated Moving Bed Technology

Two Stage Process

Purification of the crude Montelukast sodium mixture stream described hereinabove in Table 1 was carried out in a two-stage simulated moving bed (SMB) process using reverse phase simulated moving bed technology employing a nominally average size 300 micron spherical C18 particles of the invention in the stationary phase. The 300 micron spherical particles had the following properties:

| | |
|---|---|
| Average particle size (microns) | 250-500 |
| Bulk Density (gm/mL) | 0.53 |
| Surface Area ($m^2/g$) | 524 |
| Pore Volume (mL/g) | 0.83 |
| Carbon Loading (% C) | 17.5 |
| Hydrogen Loading (% H) | 3.5 |
| Solid Phase Extraction Recovery Test: (By Elution Solvent) | |
| Valerophenone Capacity (μg) | 61 |

The desorbent or mobile phase was 100 wt-% methanol, adjusted to a pH of 12 as prepared hereinabove. The crude Montelukast was converted to a crude Montelukast sodium mixture and diluted with deionized water to a concentration of 10 weight percent and adjusted by the addition of sodium hydroxide to a pH of 12 according to the above feed preparation procedure.

Stage 1 comprised a four zone system of 8 individual stationary phase adsorbent columns operating as described hereinabove with reference to FIG. 2. Each individual adsorbent filled column had an inside diameter of 20 mm and a length of 250 mm, containing 300 micron C18 adsorbent. Stage 1 was arranged in a 1-1-3-3 mode; that is, both zone 1 (301) and 2 (302) contained 3 columns, zone 4 (304) contained 1 column, and zone 3 (303) contained 1 column. Zone 3 (303) was employed to concentrate the raffinate stream. Stage 1 of the SMB process operated in rejective mode. In the rejective mode, the first raffinate stream from stage 1 was recovered and evaporated protected from light in a evaporization zone (BUECHI evaporator, available from Buechi Glas Uster AG, Switzerland) at a temperature less than 45° C. to provide an evaporated first raffinate stream having a moisture content of between 10 and 15 wt-percent. Then the evaporated first raffinate stream was passed to stage 2, that operated in and extractive mode employed 8 individual stationary phase adsorbent columns in a 2-3-3 scheme. In stage 2, zone 1 (301) contained 2 columns and zones 3 (303) and 4 (304) each contained 3 columns. In the operation of Stage 2, zones 2(302) and 3(303) are operated as a single zone. HPLC chromatographic analysis was used for the analysis of the extract and raffinate streams. The results are summarized in Table 5 as follows:

TABLE 5

SUMMARY OF TWO-STAGE SMB OPERATION W/C18

| Component: (wt-percent) | Crude Feed Stream | First Raffinate Stream | USP Grade | Second Extract Stream | Second Extract Stream (Conc.) |
|---|---|---|---|---|---|
| Montelukast Na-trans | 94.8 | 99.38 | ** | 99.51 | 99.48 |
| Montelukast Na-Sulfoxide | 1.49 | 0 | 0.1 | 0 | |
| Montelukast Na-Cis Isomer | 0.2 | 0.14 | 0.1 | 0.11 | .12 |
| Michael Adducts | 0.12 | 0.05 | 0.1 | 0 | 0 |
| Montelukast Na-Styrenic | 0.48 | 0 | 0.3 | 0 | 0 |
| Ketonic | 0.6 | 0 | 0.1 | 0 | 0 |

TABLE 5-continued

SUMMARY OF TWO-STAGE SMB OPERATION W/C18

| Component: (wt-percent) | Crude Feed Stream | First Raffinate Stream | USP Grade | Second Extract Stream | Second Extract Stream (Conc.) |
|---|---|---|---|---|---|

** Acceptance criteria: 98.0%-102.0 wt-%, on an anhydrous basis by HPLC

Thus, above two-stage scheme provided a second extract stream comprising 99.51 wt-% Montelukast sodium-trans with a level of associated impurities acceptable per USP, in a continuous process without exposing the Montelukast-trans to potential degradation in an acid medium.

The second extract stream withdrawn from stage 2 which had negligible moisture content was evaporated to dryness at a temperature of 45° C., stripped twice with heptane and crystallized with heptane as described herein above. The final purity of the solid, concentrated, recovered Montelukast sodium-trans contained 99.5 wt-% Montelukast sodium-trans.

Example 7

SMB with –25-40 Micron C18 Stationary Phase

Figure 7:
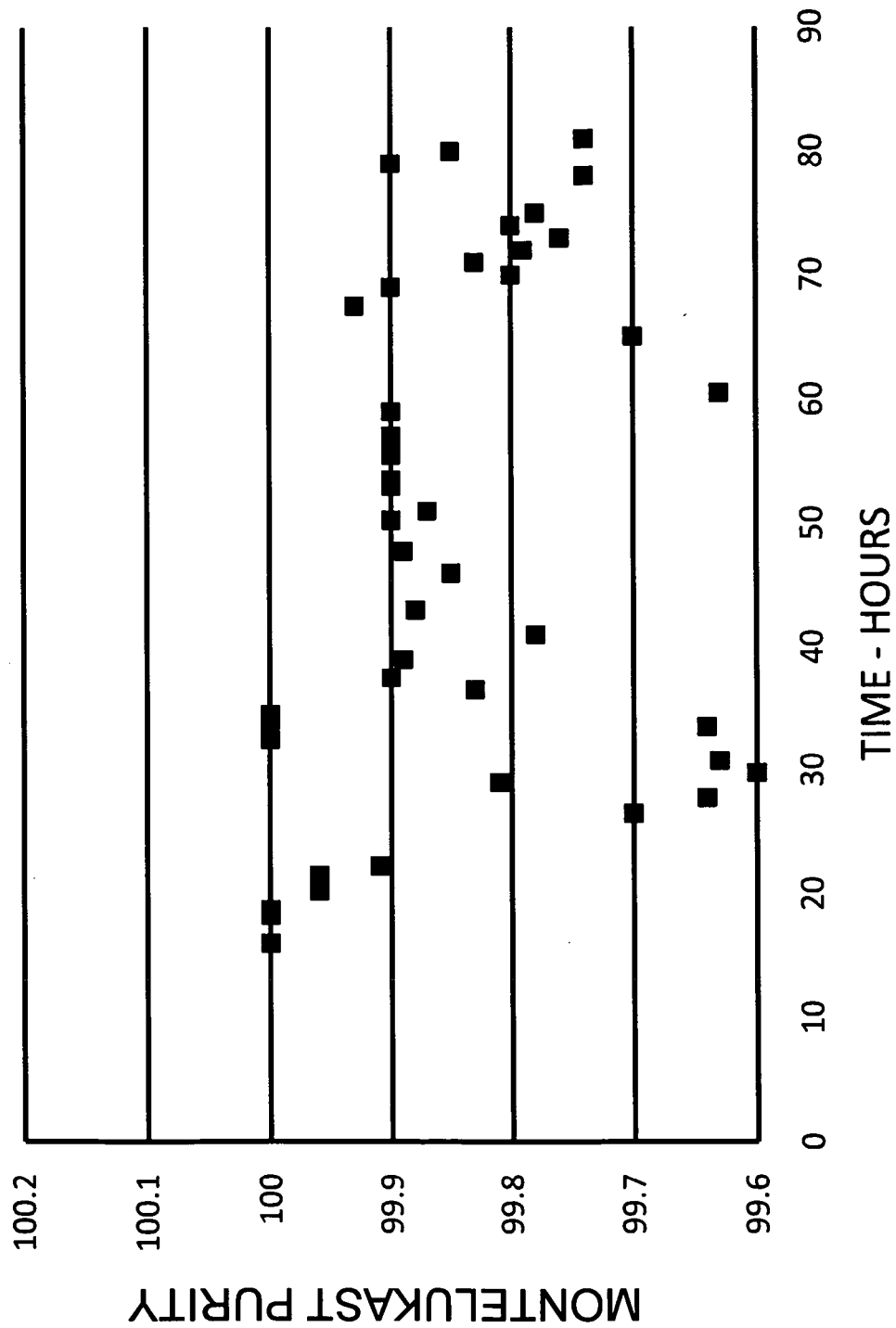
FIG. 7 is a chart of operational data showing purity of Montelukast produced from the process of the instant invention with 25 micron C18 adsorbent.
Figure 8:
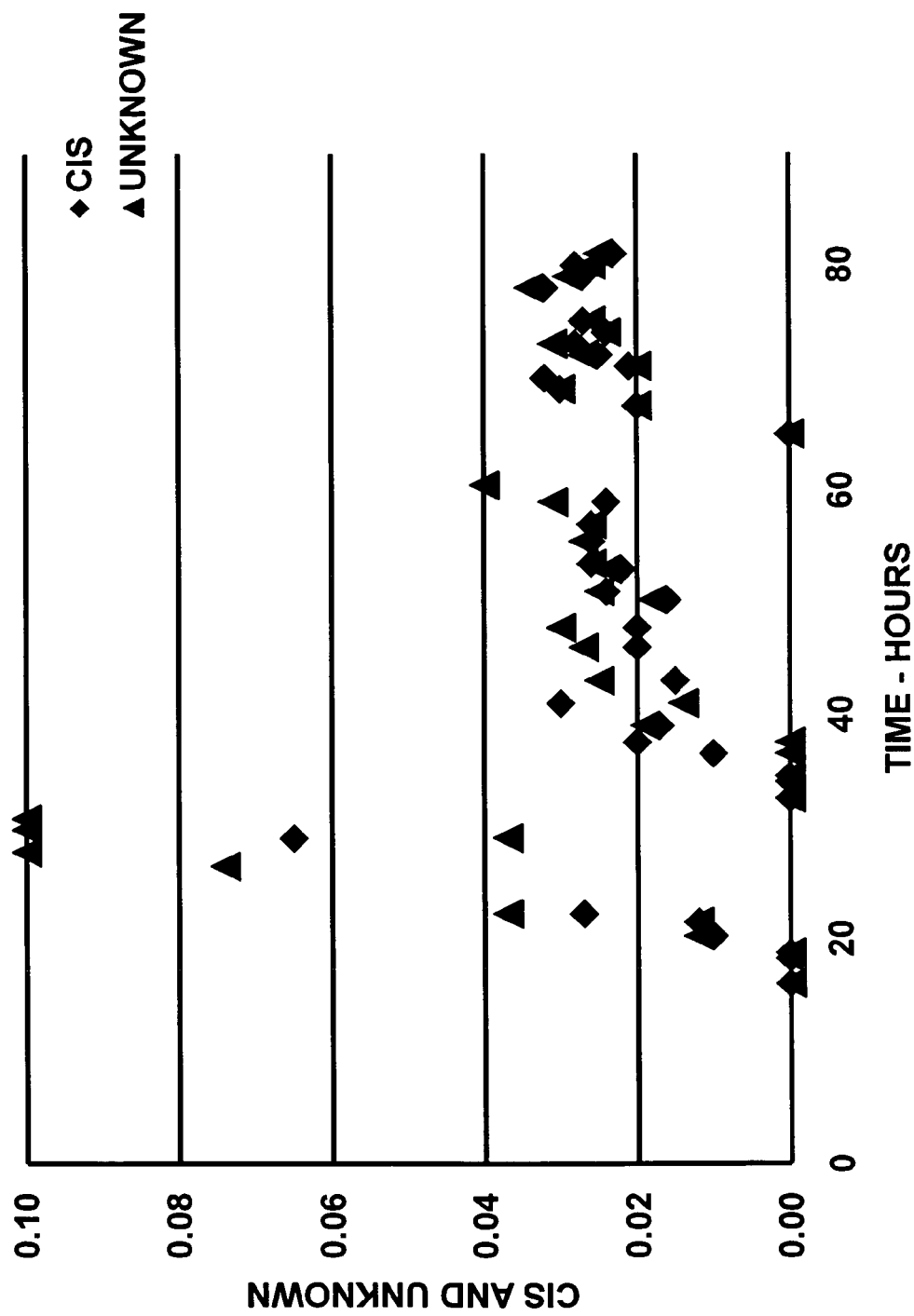
FIG. 8 a chart of operational data showing cis and unknown impurities produced from the process of the instant invention with 25 micron C18 adsorbent.

As in Example 6, a two stage SMB system using a simulated moving bed control and valve switching unit (SMB unit available from Semba Biosciences, India) was fitted with eight 22 mm I.D.×300 mm columns each packed using standard techniques with a 25 micron C18 stationary phase adsorbent (available from Orochem Technologies, Lombard, Ill.). The first stage was arranged in a 1-1-3-3 configuration. The mobile phase was 100 wt-% methanol, adjusted to a pH of about 12 with sodium hydroxide as described hereinabove. The SMB operating conditions for the first stage were:

Feed: 1 mL/min (5 wt-% Montelukast sodium in deionized water)
 Desorbent: 34 mL/min
 Extract: 20 mL/min
 Raffinate: 6 mL/min
 Cycle Time: 9 minutes The Raffinate from the first stage was passed to a second stage SMB zone, wherein eight 22 mm I.D.×300 mm columns each packed using standard techniques with a 25 micron C18 stationary phase adsorbent (available from Orochem Technologies, Lombard, Ill.). The second stage was arranged in a 2-3-3 configuration. The SMB operating conditions for the second stage were:

Feed: 4 mL/min (Raffinate from first stage)
 Desorbent: 20 mL/min
 Extract: 11.5 mL/min
 Raffinate: 12.5 mL/min
 Cycle Time: 9 minutes The Extract from the second stage SMB zone was evaporated to dryness, stripped 2 times with heptane, and crystallized with heptane as described hereinabove in Example 6. The final product purity of the Montelukast sodium-trans was 99.9 wt-% per USP analysis and no other individual impurity was present in an amount greater than 0.025 wt-%. The performance data showing the purity of the recovered second stage extract Montelukast sodium-trans is shown in FIG. 7 as a function of the position in the run. The amount of cis and unknown impurities in the second extract stream as a function of time in the run is shown in FIG. 8. A summary of the SMB operation for the C18 spherical stationary phase adsorbent having a nominal particle size of 25-40 microns is shown in Table 6.

TABLE 6

SUMMARY OF TWO-STAGE SMB OPERATION W/C18

| Component: (wt-percent) | Crude Feed Stream | First Raffinate Stream | USP Grade | Second Extract Stream | Second Extract Stream (Conc.) |
|---|---|---|---|---|---|
| Montelukast Na-trans | 94.8 | 99.38 | ** | 99.9 | 99.9 |
| Montelukast Na-Sulfoxide | 1.49 | 0 | 0.1 | 0 | |
| Montelukast Na-Cis Isomer | 0.2 | 0.14 | 0.1 | <0.025 | <0.025 |
| Michael Adducts | 0.12 | 0.05 | 0.1 | 0 | 0 |
| Montelukast Na-Styrenic | 0.48 | 0 | 0.3 | 0 | 0 |
| Ketonic | 0.6 | 0 | 0.1 | 0 | 0 |

** Acceptance criteria: 98.0%-102.0 wt-%, on an anhydrous basis by HPLC

Example 8

Evaporation of Montelukast Sodium-Trans from SMB Operation

Samples of the second extract stream from the SMB operation over the 25-40 micron stationary phase C18 adsorbent of Example 7 were collected as nine sequential samples of approximately 1.5 liters each (labeled A-I) and subjected to evaporation and extraction with heptane to form a free flowing powder. The evaporation was carried out in the absence of daylight and white light at room temperature in a ROTOVAPOR rotary vacuum evaporator (Available from Buechi Glas Uster AG, Switzerland). The samples were evaporated to dryness. Heptane was added and the rotary evaporation was continued until a powder formed and the Montelukast sodium-trans powder was free flowing. The analysis of the purified Montelukast sodium-trans second extract stream and the analysis of the resulting free flowing powder are shown hereinbelow in Table 7.

TABLE 7

Analysis of SMB Operational Data for 25-40 μm C18 Adsorbent

| Sample | Montelukast Na-trans, Purity, wt-% | Unknown wt-% | Montelukast Na-Cis-wt-% | Montelukast Na-Sulfoxide, wt-% | Montelukast Na-Styrene, wt-% |
|---|---|---|---|---|---|
| A | 99.64 | 0.026 | 0.021 | 0.017 | 0.07 |
| B | 99.76 | 0.014 | 0.025 | 0.06 | 0.057 |
| C | 99.73 | 0.018 | 0.023 | 0.06 | 0.075 |
| D | 99.7 | 0.044 | 0.053 | 0.12 | 0.04 |
| E | 99.72 | 0.029 | 0.05 | 0.13 | |
| F | 99.64 | 0.037 | 0.054 | 0.13 | 0.07 |
| G | 99.74 | 0.038 | 0.049 | 0.1 | |
| H | 99.81 | 0.024 | 0.042 | 0.076 | |
| I | 99.77 | 0.023 | 0.038 | 0.1 | |
| Ave. | 99.72 | 0.0281 | 0.0394 | 0.0881 | 0.0624 |

TABLE 7-continued

Analysis of SMB Operational Data for 25-40 µm C18 Adsorbent

Analysis of the Montelukast-trans Powder

| Montelukast Na-trans, Purity, % | Unknown wt-% | Montelukast Na-Cis-wt-% | Montelukast Na-Sulfoxide, wt-% | Montelukast Na-Styrene, wt-% |
|---|---|---|---|---|
| 99.69 | 0.033 | 0.057 | 0.1 | |

On average over the run based on the SMB process illustrated by Example 7, the SMB system produced high quality Montelukast-trans powder having a purity of about 99.7 wt-% per USP and with no known or unknown impurities individually present in excess of 0.1 wt-%.

Other embodiments are set forth within the following claims.

We claim:

1. A continuous process for the purification of a crude Montelukast sodium mixture comprising Montelukast sodium-trans and impurities comprising Montelukast sodium-cis, Montelukast sodium-sulfoxide, Montelukast sodium-styrenic impurities, other impurities, in an organic solvent to provide a purified Montelukast sodium-trans product, said process comprising:
   a. combining the crude Montelukast sodium mixture with deionized water to provide a feed mixture comprising deionized water, the organic solvent, Montelukast sodium-trans, Montelukast sodium-cis, Montelukast sodium-sulfoxide, Montelukast sodium-styrenic impurities and the other impurities, said feed mixture having a pH greater than or equal to 8.5 and less than 12, said feed mixture comprising from about 2.5 to about 10 wt-% of the crude Montelukast mixture in deionized water and filtering the feed mixture in a filtration zone to provide a filtered feed mixture;
   b. passing the filtered feed mixture and at least one mobile phase desorbent comprising methanol having a pH of between 8 and 12, to a simulated moving bed (SMB) system having a first SMB zone operating in a rejection mode and a second SMB zone operating in an extraction mode, said SMB system comprising a complex valve system and a plurality of adsorbent beds containing a stationary phase adsorbent selected from the group consisting of C4 adsorbent, C8 adsorbent, C18 adsorbent, and basic alumina and being selective for the separation of Montelukast sodium-trans from at least one of said impurities in the absence of light and at an SMB temperature of from 10 to 30° C. and at an SMB pressure effective to maintain liquid phase, wherein the stationary phase adsorbent and the at least one mobile phase desorbent are directed to flow in a counter-current manner by the complex valve system to provide a Montelukast sodium-trans rich extract stream, comprising Montelukast sodium-trans, mobile phase desorbent, and less than 0.5 wt-% water and a waste impurity stream comprising said mobile phase desorbent, Montelukast sodium-cis, Montelukast sodium-sulfoxide, the Montelukast sodium-styrenic impurities and the other impurities;
   c. passing the Montelukast sodium-trans rich extract stream comprising Montelukast sodium-trans and mobile phase desorbent to an evaporation zone operating at an evaporation temperature less than about 50° C. to recover the mobile phase desorbent and to provide an evaporated extract stream;
   d. stripping the evaporated extract stream with a hydrocarbon solvent to provide a stripped evaporated extract stream; and,
   e. passing the stripped evaporated extract stream to a crystallization zone and therein contacting the stripped evaporated extract stream with the hydrocarbon solvent selected from the group consisting of hexane, heptane, toluene and mixtures thereof at effective crystallization conditions and withdrawing the purified Montelukast sodium-trans product having a Montelukast purity of greater than or equal to 99.5 wt-%.

2. The continuous process of claim 1, wherein said other impurities comprise ketonic impurities, and Michael adducts.

3. The continuous process of claim 1, wherein the at least one mobile phase desorbent is 99 wt-% methanol adjusted to a pH of from 8.5 to 12 with sodium hydroxide.

4. The continuous process of claim 1, wherein the effective crystallization conditions of the crystallization zone comprise an effective crystallization temperature less than or equal to 15° C. and an effective crystallization pressure less than atmospheric pressure.

5. The continuous process of claim 1, wherein the complex valve system of the simulated moving bed (SMB) system simulates the movement of the stationary phase adsorbent in a direction counter-currently to the flow of at least one mobile phase desorbent, wherein said SMB system comprises the first SMB zone operated in rejective mode to provide a first extract stream comprising Montelukast sodium-styrenic impurities eluting after a Montelukast sodium-trans peak and a first raffinate stream comprising Montelukast sodium-trans, Montelukast sodium-cis, Montelukast sodium-sulfoxide, and other impurities eluting before the Montelukast sodium-trans peak, and the second SMB zone operated in extractive mode to provide a second raffinate stream comprising Montelukast sodium-cis, Montelukast sodium-sulfoxide, and said other impurities and to provide the Montelukast sodium-trans rich extract stream comprising Montelukast sodium-trans and said mobile phase desorbent.

6. The continuous process of claim 1, wherein said filtration zone comprises a 0.45 micron filter.

7. The continuous process of claim 1, further comprising passing the filtered feed mixture to a guard bed containing said stationary phase adsorbent prior to passing the filtered feed mixture to the simulated moving bed adsorption system.

8. The continuous process of claim 5, further comprising passing the first raffinate stream to a separation zone to remove at least a portion of the mobile phase desorbent prior to passing the first raffinate to the second SMB zone.

9. The continuous process of claim 8, wherein the separation zone is operated at a separation temperature less than or equal to 50° C. and a separation pressure being equal or below atmospheric pressure.

10. The continuous process of claim 8, wherein the separation zone comprises evaporation.

11. The continuous process of claim 8, wherein the separation zone comprises distillation.

12. The continuous process of claim 1, further comprising passing the waste impurity stream to a mobile phase desorbent recovery zone to recover at least a portion of the mobile phase desorbent as a recovered mobile phase desorbent and returning the recovered mobile phase desorbent to step (b) of claim 1.

13. The continuous process of claim 1, wherein the stationary phase adsorbent comprises spherical particles of a C18 adsorbent having an average particle size of from 25 to 500 microns.

14. The continuous process of claim 1, wherein the stationary phase adsorbent comprises spherical particles of a C18 adsorbent having an average particle size of from 250 to 500 microns.

15. The continuous process of claim 1, wherein the stationary phase adsorbent comprises spherical particles of a C18 adsorbent having an average particle size of from 25 to 40 microns.

16. The continuous process of claim 1, wherein the stationary phase adsorbent comprises spherical particles of a C18 adsorbent having an average particle size of from 40 to 60 microns.

17. The continuous process of claim 1, wherein the crude Montelukast sodium mixture comprises less than 95 wt-% Montelukast sodium-trans.

18. The continuous process of claim 1, wherein the stationary phase adsorbent comprises spherical particles of a C18 adsorbent comprises a carbon loading of from 15 to 20 wt-% carbon, and a hydrogen loading of from 2.5 to 5.5 wt-% hydrogen.

19. The continuous process of claim 1, wherein the stationary phase adsorbent comprises spherical particles of a C18 adsorbent having a solid phase valerophenone extraction recovery capacity of between 55 and 260 micrograms per gram capacity.

20. The continuous process of claim 1, wherein the stationary phase adsorbent comprises basic alumina.

21. The continuous process of claim 1, wherein the stationary phase adsorbent comprises a C4 adsorbent.

22. The continuous process of claim 1, wherein the stationary phase adsorbent comprises a C8 adsorbent.

23. The continuous process of claim 1, wherein the organic solvent is selected from the group consisting of methanol, $C_2$-$C_4$ alcohol, or a mixture of acetonitrile and water.

24. A continuous process for the purification of a crude Montelukast sodium mixture comprising Montelukast sodium-trans, impurities, an organic solvent, and water, wherein the impurities comprise Montelukast sodium-cis, Montelukast sodium-sulfoxide, Montelukast sodium-styrenic impurities, ketonic impurities, and Michael adducts and said crude Montelukast sodium mixture having a pH greater than or equal to 8.5 and less than 12 to provide a purified Montelukast sodium-trans product, said process comprising:
   a. diluting the crude Montelukast sodium mixture in deionized water to provide a feed mixture comprising from about 2.5 to about 10 wt-% of the crude Montelukast mixture in deionized water and filtering the feed mixture in a filtration zone having a 0.45 micron filter to provide a filtered feed mixture, said feed mixture having a pH greater than or equal to 8.5 and less than 12;
   b. passing the filtered feed mixture and a mobile phase desorbent comprising methanol having a pH of between 8 and 12 to a first SMB zone operating in a rejection mode, said first SMB zone containing a first plurality of adsorbent beds each adsorbent bed containing a stationary phase adsorbent comprising C18 spherical adsorbent having a nominal particle size of 25-40 microns and a solid phase valerophenone extraction recovery capacity of between 55 and 260 micrograms per gram capacity to provide a first extract stream comprising Montelukast sodium-styrenic impurities eluting after a Montelukast sodium-trans peak and a first raffinate stream comprising Montelukast sodium-trans, Montelukast sodium-cis, Montelukast sodium-sulfoxide, and other impurities eluting before the Montelukast sodium-trans peak;
   c) passing the first stage raffinate stream to a separation zone to provide an evaporated first stage raffinate stream,
   d) passing the evaporated first stage raffinate stream and the mobile phase desorbent comprising methanol having a pH of between 8 and 12 to a second SMB zone operating in an extraction mode, said second SMB zone containing a second plurality of adsorbent beds each adsorbent bed containing the stationary phase adsorbent comprising C18 spherical adsorbent having a nominal particle size of 25-40 microns to provide a second raffinate stream comprising Montelukast sodium-cis and Montelukast-sulfoxide and a second extract stream comprising Montelukast sodium-trans and less than about 0.1 wt-% water; and,
   d) passing the second extract stream to a drying and crystallization zone to provide a solid Montelukast sodium-trans product having a Montelukast purity of at least 99.5 wt-%.

25. The process of claim 24, wherein the solid Montelukast sodium-trans product has a has a purity of 99.5 wt-% and all impurities are within USP specification and assay 98 to 102 wt-% by HPLC on an anhydrous basis.

26. The process of claim 24, further comprising directly reacting a crude Montelukast acid mixture in the organic solvent with an inorganic base selected from the group consisting of sodium hydroxide, sodium carbonate, sodium bicarbonate, and mixtures thereof to obtain said crude Montelukast sodium mixture.

* * * * *